US007276588B2

(12) United States Patent
Pizzo et al.

(10) Patent No.: US 7,276,588 B2
(45) Date of Patent: Oct. 2, 2007

(54) ANTIBODY OF HUMAN MITOCHONDRIAL VOLTAGE DEPENDENT ANION CHANNEL

(75) Inventors: Salvatore Pizzo, Bahama, NC (US); Mario Gonzalez-Gronow, Chapel Hill, NC (US)

(73) Assignee: Duke University, Durham, NC (US)

( * ) Notice: Subject to any disclaimer, the term of this patent is extended or adjusted under 35 U.S.C. 154(b) by 624 days.

(21) Appl. No.: 10/641,340

(22) Filed: Aug. 14, 2003

(65) Prior Publication Data

US 2004/0096444 A1 May 20, 2004

Related U.S. Application Data

(60) Provisional application No. 60/403,965, filed on Aug. 16, 2002.

(51) Int. Cl.
*C07K 16/28* (2006.01)
*C07K 16/18* (2006.01)
(52) U.S. Cl. .................. 530/388.2; 530/388.1; 530/388.15
(58) Field of Classification Search .................. None
See application file for complete search history.

(56) References Cited

U.S. PATENT DOCUMENTS

| 5,780,235 | A | 7/1998 | Bandman et al. |
| 5,861,372 | A | 1/1999 | Folkman et al. |
| 6,024,688 | A | 2/2000 | Folkman et al. |
| 6,812,339 | B1 * | 11/2004 | Venter et al. ............. 536/24.31 |

FOREIGN PATENT DOCUMENTS

WO        WO99/66038        12/1999

OTHER PUBLICATIONS

Bathori et al., Porin is Present in the Plasma Membrane where it is Concentrated in Caveolae and Caveolae-related Domains, *The Journal of Biological Chemistry*, vol. 274, No. 42:29607-29612 (1999).
Bruserud et al., At Least Five Antigenic Epitopies on the Streptokinase Molecule are Recognized by Human CD4+ TCR αβ+ T Cells, *Molecular Immunology*, vol. 29, No. 9:1097-1104 (1992).
Cao et al., Expression of Angiostatin cDNA in a Murine Fibrosarcoma Suppresses Primary Tumor Growth and Produces Long-Term Dormancy of Metastases, *J. Clin. Invest.* vol. 101, No. 5:1055-1063 (Mar. 1998).
Cao et al., Kringle 5 of Plasminogen is a Novel Inhibitor of Endothelial Cell Growth, *The Journal of Biological Chemistry*, vol. 272, No. 36:22924-22928 (1997).
Coffey et al., New Antigenic Regions of Streptokinase are Identified by Affinity-Directed Mass Spectrometry, *Eur. J. Biochem*, 268:5215-5221 (2001).
Dunn et al., Monoclonal Antibodies to *Escherichia coli* $F_1$—ATPase, *Journal of Biological Chemistry*, vol. 260, No. 19:10418-10425 (1985).
Gao et al., Down-Regulation of Vascular Endothelial Growth Factor and Up-Regulation of Pigment Epithelium-Derived Factor, *The Journal of Biological Chemistry*, vol. 277, No. 11:9492-9497 (2002).
Gately et al., Human Prostate Carcinoma Cells Express Enzymatic Activity that Converts Human Plasminogen to the Angiogenesis Inhibitor, Angiostatin, *Cancer Research*, 56:4887-4890 (Nov. 1996).
Gincel et al., Calcium Binding and Translocation by the Voltage-Dependent Anion Channel: a Possible Regulatory Mechanism in Mitochondrial Function, *Biochem. J.*, 358:147-155 (2001).
Gogol et al, Cryoelectron Microscopy of *Escherichia coli* $F_1$ Adenosinetriphosphatase Decorated with Monoclonal Antibodies to Individual Subunits of the Complex, *Biochemistry*, vol. 28:4717-4724 (1989).
Gonzalez-Gronow et al., The Voltage-Dependent Anion Channel is a Receptor for Plasminogen Kringle-5 on Human Endothelial Cells, *The Journal of Biological Chemistry*, vol. 278, No. 29:27312-27318 (2003).
Gonzalez-Gronow et al., Plasminogen Activation Stimulates an Increase in Intracellular Calcium in Human Synovial Fibroblasts, *The Journal of Biological Chemistry*, vol. 268, No. 28:20791-20795 (1993).
Hajjar et al., An Endothelial Cell Receptor for Plasminogen/Tissue Plasminogen Activator, *The Journal of Biological Chemistry*, vol. 269, No. 33:21191-21197 (1994).
Ji et al., Selective Inhibition by Kringle-5 of Human Plasminogen on Endothelial Cell Migration, an Important Process in Angiogenesis, *Biochemical and Biophysical Res. Comm.*, 247:414-419 (1998).
Komatsu et al., Effect of Probucol on Intracellular pH and Proliferation of Human Vascular Endothelial Cells, *J. Pharmacol. Toxicol.* 41:33-41 (1999).
Lin et al., Epsilon Amino Caproic Acid Inhibits Streptokinase—Plasminogen Activator Complex Formation and Substrate Binding through Kringle-Dependent Mechanisms, *Biochemistry*, 39:4740-4745 (2000).
Liu et al., Angiogenesis Activators and Inhibitors Differentially Regular Caveolin-1 Expression and Caveolae Formation in Vascular Endothelial Cells, *The Journal of Biological Chemistry*, vol. 274, No. 22:15781-15785 (1999).
Lu et al., Kringle 5 Causes Cell Cycle Arrest and Apoptosis of Endothelial Cells, *Biochemical and Biophysical Res. Comm.* 258:668-673 (1999).
Lin et al., Epsilon Amino Caproic Acid Inhibits Streptokinase-Plasminogen Activator Complex Formation and Substrate Binding through Kringle-Dependent Mechanisms, *Biochemistry*, 39:4740-4745 (2000).

(Continued)

*Primary Examiner*—Michael Pak
(74) *Attorney, Agent, or Firm*—Myers Bigel Sibley & Sajovec, P.A.

(57) ABSTRACT

An isolated antibody that binds to a plasminogen kringle 5 receptor, i.e., the human voltage-dependent anion channel, preferably at an epitope between amino acids $Tyr_{224}$ through $Lys_{255}$ thereof, is described, along with methods of use thereof. Peptides or immunogens that stimulate the production of such antibodies, along with methods of use thereof, are also disclosed.

5 Claims, 7 Drawing Sheets

OTHER PUBLICATIONS

McCabe et al., Comparison of Human VDAC1 with Streptococcal Streptokinase and Bovine Bactericidal Permeability Increasing Protein: Role of Structural Information in Identifying Functionally Significant Domains, *Biochemical and Molecular Medicine*, 56:176-179 (1995).

Moradi-Ameli et al., Characterization of Monoclonal Antibodies Against Mitrochondrial $F_1$-ATPase, *Proc. Natl. Acad. Sci. USA*, 80:6167-6171 (1983).

Moser et al., The Mechanism of Action of Angiostatin: Can You Teach an Old Dog New Tricks? *Thromb Haemost*, 87:394-401 (2002).

Moser et al., Angiostatin Binds ATP Synthase on the Surface of Human Endothelial Cells, *Proc. Natl. Acad. Sci USA*, 96:2811-2816 (1999).

Nelson et al., Immunochemical Analysis of the Membrane Proteins of Rat Liver and Zajdela Hepatoma Mitochondria, *Archives of Biochemistry and Biophysics*, vol. 234, No. 1:24-30 (1984).

Nihalani et al., Streptokinase Contains Two Independent Plasminogen-Binding Sites, *Biochemical and Biophysical Res. Comm.*, vol. 217, No. 3:1245-1254 (1995).

Okamoto et al., Caveolins, a Family of Scaffolding Proteins for Organizing "Preassembled Signaling Complexes" at the Plasma Membrane, *The Journal of Biological Chemistry*, vol. 273, No. 10:5419-5422 (1998).

O'Reilly et al., Angiostatin Induces and Sustains Dormancy of Human Primary Tumors in Mice, *Nature Medicine*, vol. 2, No. 6:689-692 (1996).

Parhami-Seren et al., Structural Characterization of Immunodominant Regions of Streptokinase Recognized by Murine Monoclonal Antibodies, *Hybridoma*, vol. 15, No. 3:169-176 (1996).

Parhami-Seren et al., Mapping the Antigen Regions of Streptokinase in Humans Before and After Streptokinase Therapy, *Molecular Immunology*, vol. 32, No. 10:717-724 (1995).

Prpic et al., Role of $Na^+/H^+$ Exchange by Interferon-γ in Enhanced Expression of JE and I-$A_\beta$ Genes, *Science*, 244:469-471 (1989).

Stahl et al., The Urokinase-Type Plasminogen Activator Receptor, a GPI-Linked Protein, is Localized in Caveolae, *The Journal of Cell Biology*, vol. 129, No. 2:335-344 (1995).

Thewes et al., Ligand Interactions with the Kringle 5 Domain of Plasminogen, *The Journal of Biological Chemistry*, vol. 265, No. 7:3609-3915 (1990).

International Search Report; PCT/US03/26211; Date of Mailing Jul. 26, 2004, do not publish.

* cited by examiner

1-LN cells
bold line = anti-sk
solid line = mini-pg + anti-sk
dotted line = secondary only

ANTIBODY OF HUMAN MITOCHONDRIAL VOLTAGE DEPENDENT ANION CHANNEL

RELATED APPLICATIONS

This application claims priority under 35 U.S.C. 119(e) from U.S. Provisional Patent Application 60/403,965, filed Aug. 16, 2002, the disclosure of which is incorporated by reference herein in its entirety

GOVERNMENT SUPPORT

This invention was made with Government support under Grant Number CA-86344 from the National Cancer Institute. The Government has certain rights to this invention.

FIELD OF THE INVENTION

The present invention concerns antibodies that bind to the angiostatin Kringle 5 receptor, formulations thereof, and methods of using the same.

BACKGROUND OF THE INVENTION

Angiogenesis is a tightly regulated process and its dysregulation can lead to development and progression of diseases such as tumor growth, diabetic retinopathy, tissue and organ malformation, and cardiovascular disorders [Folkman and D'Amore, *Cell* 87, 1153 (1996); Hanahan and Folkman, *Cell* 86, 353 (1996); Folkman and Shing, *J. Biol. Chem.* 267, 10931 (1992); Folkman, *Nat. Med.* 1, 27 (1995)]. Positive angiogenic regulators include basic fibroblast growth factor (bFGF) and vascular endothelial growth factor (VEGF), which are both potent mitogens and strong chemoattractants for endothelial cells [Dusak et al., *J. Natl. Cancer Inst.* 85, 121 (1993); Kim et al., *Nature* 362, 841 (1993)]. One example of a negative regulator is angiostatin which inhibits endothelial cell proliferation in vitro and suppresses tumor growth in animals [O'Reilly et al., *Cell* 79, 315 (1994): O'Reilly et al., *Nat. Med.* 2, 689 (1996)]. Angiostatin is a fragment of plasminogen (Pg) consisting of either the first three or four of its kringles. Pg kringle 5 (K5) also suppresses growth factor-stimulated angiogenesis via cell cycle-G1 arrest and induction of apoptosis; however, the cellular receptor(s) mediating these effects are unknown [Ji et al., *Biochem. Biophys. Res. Commun* 247, 414 (1998); Y. Cao et al., *J. Biol. Chem.* 272, 22924 (1997); Y. Cao et al., *J. Clin Invest.* 101, 1055 (1998); M. Dhanabal et al., *Biochem. Biophys. Res. Commun.* 258, 668 (1999)].

K5 confers on Pg the capacity to bind to human umbilical vein endothelial cells (HUVEC) with high affinity [Wu et al., *Biochem. Biophys. Res. Commun.* 188, 703 (1992)]. K5 also mediates binding of Pg to the streptococcal Pg activator streptokinase (SK) [Nihalani and Sahni, *Biochim. Biophys. Res. Commun.* 217, 1245 (1995); Lin et al., *Biochemistry* 39, 4740 (2000), GenBank Accession No. BZSO]. Sequence similarities between SK and the mitochondrial human voltage-dependent anion channel (VDAC1) exist, but a functional relationship between these proteins has not been shown [McCabe et al., *Biochem. Mol. Med.* 56, 176 (1995)].

SUMMARY OF THE INVENTION

A first aspect of the present invention is an isolated antibody that binds to a plasminogen kringle 5 receptor, i.e., the human voltage-dependent anion channel ([Thinnes et al., *Biol. Chem. Hoppe-Seyler* 370, 1265-1278 (1989)], GenBank Accession No. AAB20246, SEQ ID NO: 1), preferably at an epitope between amino acids $Tyr_{224}$ through $Lys_{255}$ thereof. The antibody may, for example, be provided in sterile form, optionally lyophilized, for subsequent therapeutic use.

A second aspect of the present invention is a pharmaceutical formulation comprising an antibody as described above in a pharmaceutically acceptable carrier.

A further aspect of the present invention is a method of inhibiting angiogenesis in a subject in need thereof, comprising administering an antibody as described above to that subject in an amount effective to inhibit angiogenesis.

A further aspect of the present invention is a method of inhibiting endothelial cell proliferation in a subject in need thereof, comprising administering an antibody as described above to that subject in an amount effective to inhibit endothelial cell proliferation.

A still further aspect of the present invention is a method of treating cancer or a tumor (i.e., one or more tumors) in a subject in need thereof, comprising administering an antibody as described above to that subject in an amount effective to treat the cancer or tumor.

The foregoing methods of treatment can be carried out directly by administering an antibody or indirectly by administering a peptide mimetic of the region to which the antibody binds, which in turn induces an immune response that stimulates the production of autoantibodies that bind to the kringle 5 receptor in the region described above.

Thus, a further aspect of the present invention is a peptide or immunogen that binds to an antibody, which antibody binds to the human mitochondrial voltage-dependent anion channel protein of SEQ ID NO: 1 at an epitope between amino acids $Tyr_{224}$ through $Lys_{255}$ thereof. Typically such peptides are at least 3, 4 or 5 amino acids in length. Such peptides may optionally be coupled to a carrier or adjuvant in accordance with known techniques.

A further aspect of the present invention is a pharmaceutical formulation comprising an peptide as described above in a pharmaceutically acceptable carrier (e.g., an aqueous carrier).

A further aspect of the invention is a method of inhibiting angiogenesis in a subject in need thereof, comprising administering a peptide as described above to the subject in an amount effective to inhibit angiogenesis.

A still further aspect of the invention is a method of inhibiting endothelial cell proliferation in a subject in need thereof, comprising administering a peptide as described above to said subject in an amount effective to inhibit endothelial cell proliferation.

A still further aspect of the invention is a method of treating cancer or tumor(s) in a subject in need thereof, comprising administering a peptide as described above to said subject in an amount effective to treat the cancer or tumor(s).

A still further aspect of the present invention is the use of an antibody or peptide as described above for the preparation of a medicament for carrying out a method as described above.

The foregoing and other objects and aspects of the present invention are explained in greater detail in the drawings herein and the specification set forth below.

BRIEF DESCRIPTION OF THE DRAWINGS

FIG. 2A. $^{125}$I-K5 (30 ng) filtered through the column.

FIG. 2B. $^{125}$I-K5 (30 ng) reacted with VDAC1 (2 μg) and then filtered through the column.

FIG. 2C. VDAC1 (2 μg) incubated with pre-assembled liposomes in 5% DMSO with agitation for 30 min. At this time, the concentration of DMSO was reduced to 0.5% by addition of $^{125}$I-K5 (30 ng) in 50 mM Tris-HCl, pH 7.5, incubated with agitation for another 30 min, followed by gel filtration.

FIG. 2D. Conditions were identical to those described in FIG. 2C, except that the mixture of VDAC1 and liposomes was incubated for 30 min with a rabbit anti-VDAC1 (peptide $Lys_{235}$-$Lys_{255}$) IgG before addition of $^{125}$I-K5 and gel filtration.

FIG. 3A. HUVEC incubated with a rabbit anti-SK (peptide $Glu_{263}$-$Lys_{283}$) IgG.

FIG. 3B. HUVEC incubated with a rabbit anti-VDAC1 (peptide $Lys_{235}$-$Lys_{255}$) IgG.

FIG. 3C. HUVEC incubated with a murine anti-mitochondrial VDAC1.

FIG. 5A. Effect of Pg 2 on [Ca$^{2+}$]$_i$.

FIG. 5B. Effect of Pg 2 on [pH]$_i$.

FIG. 5C. Effect of K5 on [Ca$^{2+}$]$_i$.

FIG. 5D. Effect of K5 on [pH]$_i$.

FIG. 5E. Effect of addition of K5 (180 s) followed by Pg 2 (340 s) on [Ca$^{2+}$]$_i$.

FIG. 5F. Effect of addition of K5 followed by Pg 2 on [pH]$_i$.

FIG. 6A. Effect of increasing concentrations of the SK peptide containing the amino acid sequence $Glu_{263}$-$Lys_{283}$ (filled squares) or the VDAC1 peptide containing the amino acid sequence $Lys_{235}$-$Lys_{255}$ (filled triangles).

FIG. 6B. Effect of increasing concentrations of the SK peptides containing the amino acid sequences $Asp_{128}$-$Asp_{137}$ (filled squares) or $Asp_{382}$-$Ile_{392}$ (filled triangles).

FIG. 7A. Cells were incubated in PRMI 1640 culture medium and exposed to the calcium chelating agent FURA 2/AM for 20 min. At this time, the cells were installed in a micro-chamber under the fluorescent microscope and incubated with serum-free RPMI 1640 until an stable base line was obtained. K5 (0.1 μM) was added at this time and the response was measured for 300 s.

FIG. 7B. Cells were incubated with the anti-SK-peptide IgG before addition of K5.

DETAILED DESCRIPTION OF THE PREFERRED EMBODIMENTS

Figure 1:
FIG. 1A. VDAC1 amino acid sequence similarities with SK identified with the BLAST program provided by the Swiss-Protein Network Service.
FIG. 1B. Hidden Markov model of VDAC1, which shows a transmembrane domain forming a loop through the outer membrane homologous to SK.
Figure 1:
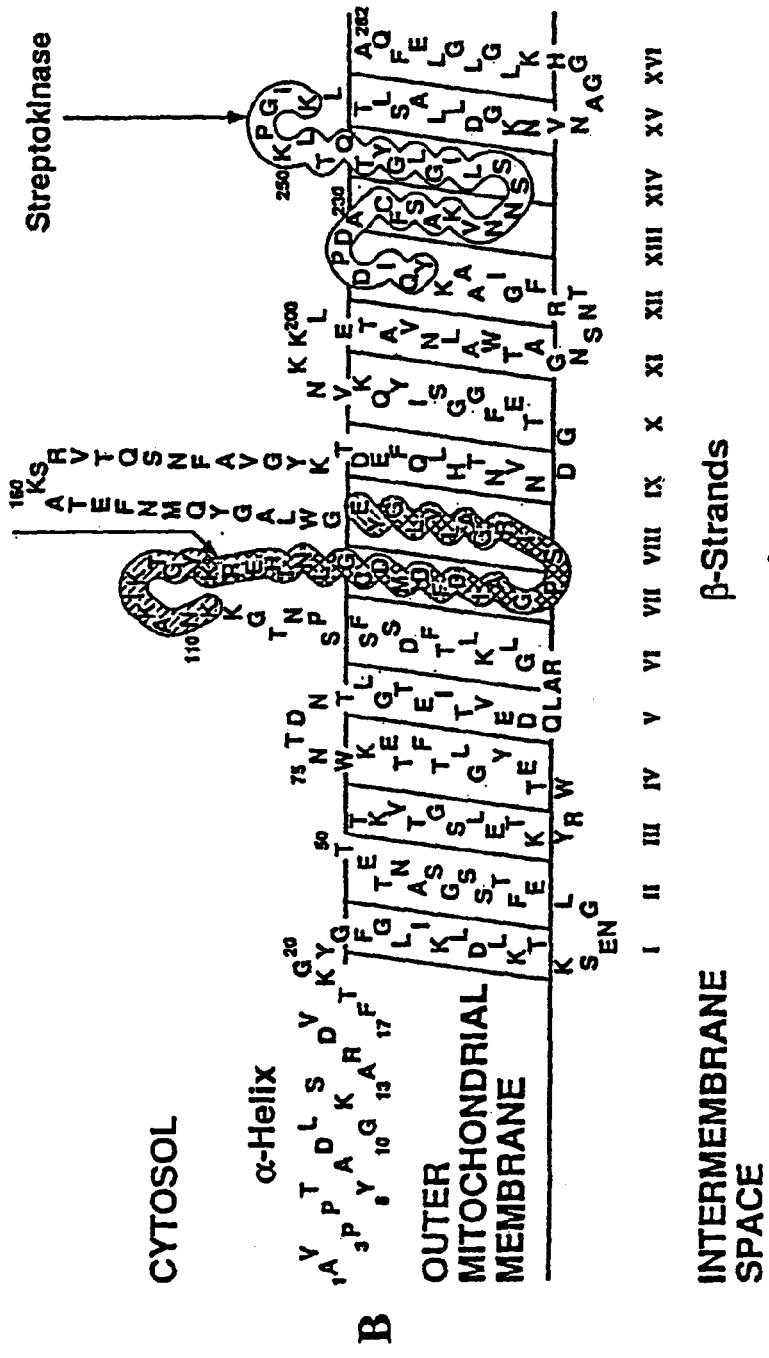

1. Definitions.

Subjects with which the present invention may be carried out are generally mammalian subjects, including both human subjects and non-human subjects (e.g., dog, cat, horse, rabbit, rat) for veterinary or research purposes.

"Epitope" as used herein refers to a discrete region of a protein or peptide, typically at least 3 to 4 continuous amino acids in length, to which an antibody specifically binds.

The term "antibodies" as used herein refers to all types of immunoglobulins, including IgG, IgM, IgA, IgD, and IgE. The antibodies may be monoclonal or polyclonal (with monoclonal antibodies preferred), may be of any species of origin, including (for example) mouse, rat, rabbit, horse, or human. See, e.g., M. Walker et al. *Molec. Immunol.* 26, 403-11 (1989), may be substituted or unsubstituted, and may be naturally occurring or synthetics. Antibody fragments that retain specific binding to the epitope bound by the antibody are included within the scope of the term "antibody" and include, for example. Fab, F(ab')2, and Fc fragments, and the corresponding fragments obtained from antibodies other than IgG. Such fragments can be produced by known techniques. The antibodies may be chimeric or humanized, particularly when they are used for therapeutic purposes. Antibodies may be coupled to detectable or therapeutic groups if so desired.

Applicants specifically intend that all United States patent references cited herein be incorporated herein by reference in their entirety.

2. Antibodies.

Polyclonal antibodies used to carry out the present invention may be produced in accordance with known techniques in light of the disclosure provided herein. In general, such antibodies may be produced by immunizing a suitable animal (e.g., rabbit, goat, etc.) with the antigen to which the monoclonal antibody binds, collecting immune serum from the animal, and separating the polyclonal antibodies from the immune serum, in accordance with known procedures. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

Monoclonal antibodies of the present invention may be prepared using any technique which provides for the production of antibody molecules by continuous cell lines in culture. These include, but are not limited to, the hybridoma technique, the human B-cell hybridoma technique, and the EBV-hybridoma technique [Kohler et al., *Nature* 256:495-497 (1975); Kozbor et al *J. Immunol. Methods* 81:31-42. (1985); Cote et al., *Proc. Natl. Acad. Sci.* 80:2026-2030 (1983); Cole et al., *Mol. Cell Biol.* 62:109-120 (1984)]. Briefly, the procedure is as follows: an animal is immunized with antigen. Lymphoid cells (e.g. splenic lymphocytes) are then obtained from the immunized animal and fused with immortalizing cells (e.g. myeloma or heteromyeloma) to produce hybrid cells. The hybrid cells are screened to identify those which produce the desired antibody.

Human hybridomas which secrete human antibody can be produced by the Kohler and Milstein technique. Although human antibodies are especially preferred for treatment of human, in general, the generation of stable human-human hybridomas for long-term production of human monoclonal antibody can be difficult. Hybridoma production in rodents, especially mouse, is a very well established procedure and thus, stable murine hybridomas provide an unlimited source of antibody of select characteristics. As an alternative to human antibodies, the mouse antibodies can be converted to chimeric murine/human antibodies by genetic engineering techniques. See V. T. Oi et al. *BioTechniques* 4:214-221 (1986); L. K. Sun et al. *Hybridoma* 5 (1986).

In addition, techniques developed for the production of "chimeric antibodies", the splicing of mouse antibody genes to human antibody genes to obtain a molecule with appropriate antigen specificity and biological activity can be used [Morrison, et al., *Proc. Natl. Acad. Sci.* 81, 6851-6855 (1984); Neuberger et al., *Nature* 312:604-608 (1984); Takeda et al., *Nature* 314:452-454 (1985)]. Alternatively, techniques described for the production of single chain antibodies may be adapted, using methods known in the art, to produce isoform-specific single chain antibodies. Antibodies with related specificity, but of distinct idiotypic composition, may be generated by chain shuffling from random combinatorial immunoglobin libraries [Burton, *Proc. Natl. Acad. Sci.* 88,11120-3 (1991)].

Antibodies may also be produced by inducing in vivo production in the lymphocyte population or by screening immunoglobulin libraries or panels of highly specific binding reagents as disclosed in the literature [Orlandi et al., *Proc. Natl. Acad. Sci.* 86, 3833-3837 (1989)); Winter et al., *Nature* 349, 293-299 (1991)].

Antibodies that selectively bind to a particular receptor or epitope as described herein can be identified in accordance with known techniques, such as their ability to compete with Kringle 5 in binding to that receptor in a competitive binding assay.

3. Therapeutic Antibodies and Methods.

Antibodies used for therapy (e.g., in a method of combating cancer) may be of any suitable form, including polyclonal antibodies, monoclonal antibodies, chimeric antibodies, etc.

Although the antibodies are useful per se due to their competitive binding activity, the antibodies may optionally be coupled to a therapeutic agent. When used for therapy such antibodies are referred to herein as therapeutic antibodies. Any therapeutic agent conventionally coupled to an antibody may be employed, including (but not limited to) radioisotopes, cytotoxic agents, and chemotherapeutic agents (See generally *Monoclonal Antibodies and Cancer Therapy* [Reisfeld and Sell Eds. 1985)(Alan R. Liss Inc. NY); U.S. Pat. No. 5,558,852 to Bigner and Zalutsky; U.S. Pat. No. 5,624,659 to Bigner and Zalutsky].

Therapeutic agents may be conjugated or coupled to the antibody by direct means or indirect means (e.g., via a chelator), such as the Iodogen method or with N-succinimidyl-3-(tri-n-butylstanyl)benzoate (the "ATE method"), as will be apparent to those skilled in the art. See, e.g., Zalutsky and Narula, *Appl. Radiat. Isot.* 38, 1051 (1987). In addition, detectable groups may be coupled to the antibodies and the antibodies used for diagnostic purposes in accordance with standard techniques.

Examples of radioisotopes which may be coupled to a therapeutic antibody include, but are not limited to, $^{131}$I, $^{90}$Y, $^{211}$At, $^{212}$Bi, $^{67}$Cu, $^{186}$Re, $^{188}$Re, and $^{212}$Pb. Examples of chemotherapeutic agents which may be coupled to a therapeutic monoclonal antibody include, but are not limited to, methotrexate. Examples of cytotoxic agents which may be coupled to a therapeutic monoclonal antibody include, but are not limited to, ricin (or more particularly the ricin A chain).

Therapeutic monoclonal antibodies may be provided in lyophylized form in a sterile aseptic container or may be provided in a pharmaceutical formulation in combination with a pharmaceutically acceptable carrier, such as sterile pyrogen-free water or sterile pyrogen-free physiological saline solution.

For administration, the antibody will generally be mixed, prior to administration, with a non-toxic, pharmaceutically acceptable carrier substance (e.g. normal saline or phosphate-buffered saline), and may be administered using any medically appropriate procedure, e.g., intravenous or intra-arterial administration, injection into the cerebrospinal fluid). The antibody may be included in the formulation in any suitable amount, for example from 0.01 or 0.5 to 95 or 99 percent by weight or more. In certain cases, intradermal, intracavity, intrathecal or direct administration to the tumor or to an artery supplying the tumor is advantageous.

Dosage of the antibody will depend, among other things, on the tumor or disorder being treated, the route of administration, the nature, if any, of the therapeutic agent employed, and the sensitivity of the tumor to the particular therapeutic agent. For example, the dosage will typically be about 1 to 10 micrograms per Kilogram subject body weight. The antibody can be administered to the subject in a series of more than one administration, and regular periodic administration will sometimes be required.

Antibodies of the present invention may be used to treat the same disorders suggested for treatment with Angiostatin in U.S. Pat. No. 6,024,688 to Folkman et al., at columns 19-20. Thus the present invention includes the method of treating an angiogenesis mediated disease with an effective amount of an antibody as described herein. The angiogenesis mediated diseases include, but are not limited to, solid tumors; blood born tumors such as leukemias; tumor metastasis; benign tumors, for example hemangiomas, acoustic neuromas, neurofibromas, trachomas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation. Antibodies of the invention are also useful in the treatment of disease of excessive or abnormal stimulation of endothelial cells. These diseases include, but are not limited to, intestinal adhesions, Crohn's disease, atherosclerosis, scleroderma, and hypertrophic scars, i.e., keloids. Antibodies of the invention can be used as a birth control agent by preventing vascularization required for embryo implantation. Antibodies of the invention are useful in the treatment of diseases that have angiogenesis as a pathologic consequence such as cat scratch disease (Rochele minalia quintosa) and ulcers (*Helicobacter pylori*).

In addition, the antibodies of the invention bind to the K5 receptor with high specificity and avidity and can be radiolabeled and employed for visualization and quantitation of binding sites using autoradiographic and membrane binding techniques. This application provides important diagnostic and research tools. Knowledge of the binding properties of the angiostatin receptor facilitates investigation of the transduction mechanisms linked to the receptor.

In addition, antibodies of the invention labeled with short lived isotopes can be used for the visualization of receptor binding sites in vivo using positron emission tomography or other modern radiographic techniques to locate tumors with angiostatin binding sites.

4. Peptides.

An alternate embodiment of the present invention involves administering a peptide mimetic of the epitope described above in an amount effective to induce an immune response thereto, the immune response resulting in the production (and hence self-administration) of antibodies (i.e., autoantibodies) as described above in an amount effective to the carry out the methods described above.

In protein molecules which interact with a receptor, the interaction between the protein and the receptor must take place at surface-accessible sites in a stable three-dimensional molecule. By arranging the critical binding site residues in an appropriate conformation, peptides which mimic the essential surface features of the epitope described herein may be designed and synthesized in accordance with known techniques, such as described in U.S. Pat. No. 5,604,203 to Balasubramaniam, the disclosure of which is incorporated by reference herein in its entirety.

Methods for determining peptide three-dimensional structure and analogs thereto are known, and are sometimes referred to as "rational drug design techniques". See, e.g., U.S. Pat. No. 4,833,092 to Geysen; U.S. Pat. No. 4,859,765 to Nestor; U.S. Pat. No. 4,853,871 to Pantoliano; U.S. Pat. No. 4,863,857 to Blalock; (applicants specifically intend that the disclosures of all U.S. Patent references cited herein be incorporated by reference herein in their entirety).

In general, those skilled in the art will appreciate that minor deletions or substitutions may be made to the amino acid sequences of peptides of the present invention without unduly adversely affecting the activity thereof Thus, peptides containing Such deletions or substitutions are a further aspect of the present invention. In peptides containing substitutions or replacements of amino acids, one or more amino acids of a peptide sequence may be replaced by one or more other amino acids wherein such replacement does not affect the function of that sequence. Such changes can be guided by known similarities between amino acids in physical features such as charge density, hydrophobicity/hydrophilicity, size and configuration, so that amino acids are substituted with other amino acids having essentially the same functional properties. For example:

Ala may be replaced with Val or Ser;

Val may be replaced with Ala, Leu, Met, or Ile, preferably Ala or Leu;

Leu may be replaced with Ala, Val or Ile, preferably Val or lie;

Ile may be replaced with Ala, Val or Leu, preferably Val or Leu;

Gly may be replaced with Pro or Cys, preferably Pro;

Pro may be replaced with Gly, Cys, Ser, or Met, preferably Gly, Cys, or Ser;

Cys may be replaced with Gly, Pro, Ser, or Met, preferably Pro or Met;

Met may be replaced with Pro or Cys, preferably Cys;

His may be replaced with Phe or Gin, preferably Phe;

Phe may be replaced with His, Tyr, or Trp, preferably His or Tyr;

Tyr may be replaced with His, Phe or Trp, preferably Phe or Trp;

Trp may be replaced with Phe or Tyr, preferably Tyr;

Asn may be replaced with Gin or Ser, preferably Gln;

Gln may be replaced with His, Lys, Glu, Asn, or Ser, preferably Asn or Ser;

Ser may be replaced with Gln, Thr, Pro, Cys or Ala;

Thr may be replaced with Gln or Ser, preferably Ser;

Lys may be replaced with Gln or Arg;

Arg may be replaced with Lys, Asp or Glu, preferably Lys or Asp;

Asp may be replaced with Lys, Arg, or Glu, preferably Arg or Glu; and

Glu may be replaced with Arg or Asp, preferably Asp.

Once made, changes can be routinely screened to determine their effects on function with the antibodies described herein.

As set forth above and for convenience in describing this invention, the conventional and non-conventional abbreviations for the various amino acids are used. They are familiar to those skilled in the art, but for clarity are listed below:

Asp=D=Aspartic Acid
Ala=A=Alanine
Arg=R=Arginine
Asn=N=Asparagine
Cys=C=Cysteine
Gly=G=Glycine
Glu=E=Glutamic Acid
Gln=Q=Glutamine
His=H=Histidine
Ile=I=Isoleucine
Leu=L=Leucine
Lys=K=Lysine
Met=M=Methionine
Phe=F=Phenylalanine
Pro=P=Proline
Ser=S=Serine
Thr=T=Threoninie
Trp=W=Tryptophan
Tyr=Y=Tyrosine
Val=V=Valine All peptide sequences mentioned herein are written according to the usual convention whereby the N-terminal amino acid is on the left and the C-terminal amino acid is on the right. A short line (or no line) between two amino acid residues indicates a peptide bond.

Peptides that may be used to carry out the present invention include compounds of Formula I:

wherein:

$A_1$ is present or absent and when present is Gln, His, Lys, Glu, Asn, or Ser, preferably Gln, Asn, or Ser, most preferably Gln (corresponding to VDAC position 248);

$A_2$ is present or absent and when present is Thr, Gln, or Ser, preferably Thr or Ser, most preferably Thr (corresponding to VDAC position 249);

$A_3$ is present or absent and when present is Leu, Ala, Val or Ile, preferably Leu, Val or Ile, most preferably Leu (corresponding to VDAC position 250);

$A_4$ is present or absent and when present is Lys, Gln or Arg, most preferably Lys (corresponding to VDAC position 251);

$A_5$ is present or absent and when present is Pro, Gly, Cys, Ser or Met, preferably Pro, Gly, Cys, or Ser, most preferably Pro (corresponding to VDAC position 252);

$A_6$ is present or absent and when present is Gly, Pro or Cys, preferably Gly or Pro, most preferably Gly (corresponding to VDAC position 253);

$A_7$ is present or absent and when present is Ile, Ala, Val or Leu, Preferably Ila, Val or Leu, most preferably Ile (corresponding to VDAC position 254);

$A_8$ is present or absent and when present is Lys, Gln or Arg, most preferably Lys (corresponding to VDAC position 255);

$A_9$ is present or absent and when present is Leu, Ala, Val or Ile, preferably Leu, Val or Ile, most preferably Leu (corresponding to VDAC position 256);

subject to the proviso or condition that at least 3, 4 or 5 consecutive ones of Al through $A_9$ are always present or included in the polypeptide chain formed by $A_1$ through $A_9$;

X is present or absent and when present is a chain of 1 to 5, 10, 15, 20 or 25 amino acids (i.e., a polypeptide), the N-terminal one of which is optionally bonded to $R_1$ and $R_2$;

Y is present or absent and when present is a chain of I to 5, 10, 15, 20 or 25 amino acids (i.e., a polypeptide), the C-terminal one of which is optionally bonded to $R_3$ and $R_4$;

$R_1$ when present is H, C1-C12 alkyl (e.g., methyl), C6-C18 aryl (e.g., phenyl, naphthaleneacetyl), C1-C12 acyl (e.g., formyl, acetyl, and myristoyl), C7-C18 aralkyl (e.g., benzyl), or C7-C18 alkaryl (e.g., p-methylphenyl);

$R_2$ when present is H, C1-C12 alkyl (e.g., methyl), C6-C18 aryl (e.g., phenyl, naphthaleneacetyl), C1-C12 acyl (e.g., formyl, acetyl, and myristoyl), C7-C18 aralkyl (e.g., benzyl), or C7-C18 alkaryl (e.g., p-methylphenyl);

$R_3$ when present is H, C1-C12 alkyl (e.g., methyl), C6-C18 aryl (e.g., phenyl, naphthaleneacetyl), C1-C12 acyl (e.g., formyl, acetyl, and myristoyl), C7-C18 aralkyl (e.g., benzyl), or C7-C18 alkaryl (e.g., p-methylphenyl); and $R_4$ when present is H, C1-C12 alkyl (e.g., methyl), C6-C18 aryl (e.g., phenyl, naphthaleneacetyl), C1-C12 acyl (e.g., formyl, acetyl, and myristoyl), C7-C18 aralkyl (e.g., benzyl), or C7-C18 alkaryl (e.g., p-methylphenyl);

or a pharmaceutically acceptable salt thereof.

Non-limiting examples of compounds of Formula I are: QTLKPGIKL (SEQ ID NO: 5), NTLKPGIKL (SEQ ID NO: 6), QSLKPGIKL (SEQ ID NO: 7), QTIKPGIKL, (SEQ ID NO: 8), QTLRPGIKL (SEQ ID NO: 9), QTLKGGIKL (SEQ ID NO: 10), QTLKPPIKL (SEQ ID NO: 11), QTLKPGLKL (SEQ ID NO: 12), QTLKPGIRL (SEQ ID NO: 13), QTLKPGIKI (SEQ ID NO: 14), HTLKPGIKL (SEQ ID NO: 15), KTLKPGIKL (SEQ ID NO: 16), ETLKPGIKL (SEQ ID NO: 17), STLKPGIKL (SEQ ID NO: 18), QQLKPGIKL (SEQ ID NO: 19), QTVKPGIKL (SEQ ID NO: 20), QTAKPGIKL (SEQ ID NO: 21), QTLQPGIKL (SEQ ID NO: 22), QTLKCGIKL (SEQ ID NO: 23), QTLKSGIKL (SEQ ID NO: 24), QTLKMGIKL (SEQ ID NO: 25), QTLKPCIKL (SEQ ID NO: 26), QTLKPGVKL (SEQ ID NO: 27) QTLKPGAKL (SEQ ID NO: 28), QTLKPGIQL (SEQ ID NO: 29), QTLKPGIKV (SEQ ID NO: 30) QTLKPGIKA (SEQ ID NO: 31), NSLKPGIKL (SEQ ID NO: 32), NQLKPGIKL (SEQ ID NO: 33), HSLKPGIKL (SEQ ID NO: 34), HQLKPGIKL (SEQ ID NO: 35) and SQLKPGIKL (SEQ ID NO: 36). Further non-limiting examples of compounds of Formula I are 3, 4, 5, 6, 7 or 8 consecutive amino acids from any of SEQ ID NOS: 5-36.

Peptides that may be used to carry out the present invention also include compounds of Formula II:

wherein:

$A_{11}$ is present or absent and when present is Asp, Lys, Arg or Glu, preferably Asp, Arg, or Glu, most preferably Asp (corresponding to VDAC position 227);

$A_{12}$ is present or absent and when present is Pro, Gly, Cys, Ser or Met, preferably Pro, Gly, Cys, or Ser, most preferably Pro (corresponding to VDAC position 228);

$A_{13}$ is present or absent and when present is Asp, Lys, Arg or Glu, preferably Asp, Arg, or Glu, most preferably Asp (corresponding to VDAC position 229);

$A_{14}$ is present or absent and when present is Ala, Val or Ser, most preferably Ala (corresponding to VDAC position 230);

subject to the proviso or condition that at least 3 consecutive ones, or all 4, of $A_1$, through $A_{14}$ are always present or included in the polypeptide chain formed by $A_1$ through $A_9$ (TYPO—This is supposed to be $A_{11}$ through $A_{14}$);

X' is present or absent and when present is a chain of 1 to 5, 10, 15, 20 or 25 amino acids (i.e., a polypeptide), the N-terminal one of which is optionally bonded to $R_{11}$ and $R_{12}$;

Y' is present or absent and when present is a chain of 1 to 5, 10, 15, 20 or 25 amino acids (i.e., a polypeptide), the C-terminal one of which is optionally bonded to $R_{13}$ and $R_{14}$;

$R_{11}$ when present is H, C1-C12 alkyl (e.g., methyl), C6-C18 aryl (e.g., phenyl, naphthaleneacetyl), C1-C12 acyl (e.g., formyl, acetyl, and myristoyl), C7-C18 aralkyl (e.g., benzyl), or C7-C18 alkaryl (e.g., p-methylphenyl);

$R_{12}$ when present is H, C1-C12 alkyl (e.g., methyl), C6-C18 aryl (e.g., phenyl, naphthaleneacetyl), C1-C12 acyl (e.g., formyl, acetyl, and myristoyl), C7-C18 aralkyl (e.g., benzyl), or C7-C18 alkaryl (e.g., p-methylphenyl);

$R_{13}$ when present is H, C1-C12 alkyl (e.g., methyl), C6-C18 aryl (e.g., phenyl, naphthaleneacetyl), C1-C12 acyl (e.g., formyl, acetyl, and myristoyl), C7-C18 aralkyl (e.g., benzyl), or C7-C18 alkaryl (e.g., p-methylphenyl); and $R_{14}$ when present is H, C1-C12 alkyl (e.g., methyl), C6-C18 aryl (e.g., phenyl, naphthaleneacetyl), C1-C12 acyl (e.g., formyl, acetyl, and myristoyl), C7-C18 aralkyl (e.g., benzyl), or C7-C18 alkaryl (e.g., p-methylphenyl);

or a pharmaceutically acceptable salt thereof.

Non-limiting examples of compounds of Formula II are: DPDA (SEQ ID NO: 37), EPDA (SEQ ID NO: 38), DGDA, (SEQ ID NO: 39), DPEA, (SEQ ID NO: 40). DPDV (SEQ ID NO: 41), KPDA, (SEQ ID NO: 42), RPDA (SEQ ID NO: 43), DCDA (SEQ ID NO: 44), DSDA (SEQ ID NO: 45), DMDA (SEQ ID NO: 46), DPKA (SEQ ID NO: 47), DPRA, (SEQ ID NO: 48), DPDS (SEQ ID NO: 49), EGDA (SEQ ID NO: 50), DPES (SEQ ID NO: 51), EPEA (SEQ ID NO: 52), DSEA (SEQ ID NO: 53), EPDS (SEQ ID NO: 54), DGDS (SEQ ID NO: 55), DPEV (SEQ ID NO: 56), RGDA (SEQ ID NO: 57), RPEA (SEQ ID NO: 58) and RPDS (SEQ ID NO: 59). Further non-limiting examples of compounds of Formula II are 3 consecutive amino acids from any of SEQ ID NOS: 37-59.

In general, The symbol X, Y, Z, $A_1$, $A_2$, $A_3$, and the like; and Ser, Leu or the like, as found in a peptide sequence herein stands for an amino acid residue, i.e., =N—CH(R)—CO— when it is at the N-terminus, or —NH—CH(R)—CO—N= when it is at C-terminus, or —NH—CH(R)—CO— when it is not at the N-or C-terminus, where R denotes the side chain (or identifying group) of an amino acid or its residue. For example, R is —CH2 COOH for Asp, R is —H for Gly, R is —CH$_2$ OH for Ser, R is —CH3 for Ala and R is —CH$_2$CH$_2$CH$_2$CH$_2$NH$_2$ for Lys. Also, when the amino acid residue is optically active, it is the L-form configuration that is intended unless the D-form is expressly designated.

If desired, the peptides used to induce an immune response may be conjugated to or coupled to a carrier, such as described in U.S. Pat. No. 6,403,092, the disclosure of which is incorporated herein by reference in its entirety.

In addition, the compounds of Formula I or Formula II may have at least one pseudopeptide bond between amino acid residues. By "pseudopeptide bond" is meant that the carbon atom participating in the bond between two residues is reduced from a carbonyl carbon to a methylene carbon, i.e., CH$_2$—NH; or less preferably that of CO—NH is replaced with any of CH$_2$—S, CH$_2$—CH$_2$, CH$_2$—O, or CH$_2$—CO. A detailed discussion of the chemistry of pseudopeptide bonds is given in Coy et al. (1988) *Tetrahedron* 44:835-841.

Peptides of the present invention may be made in accordance with techniques known in the art. Using accepted techniques of chemical synthesis, the peptide may be built up either from the N-terminus or, more typically, the C-terminus using either single amino acids or preformed peptides containing two or more amino acid residues. Particular techniques for synthesizing peptides include (a) classical methods in which peptides of increasing size are isolated before each amino acid or preformed peptide addition, and (b) solid phase peptide synthesis in which the peptide is built up attached to a resin such as a Merrifield resin. In these synthetic procedures, groups on the amino acids will generally be in protected form using standard protecting groups such as t-butoxycarbonyl. If necessary, these protecting groups are cleaved once the synthesis is complete. Other modifications may be introduced during or after the synthesis of the peptide. Peptides of the present invention may also be produced through recombinant DNA procedures as are known in the art.

5. Peptide Formulations and Methods.

Peptide active compounds of the present invention may be used for the same methods of treatment as described above in connection with antibodies.

The active compound peptides disclosed herein can, as noted above, be prepared and administered in the form of their pharmaceutically acceptable salts. Pharmaceutically acceptable salts are salts that retain the desired biological activity of the parent compound and do not impart excessive toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

The active compounds described above may be formulated for administration in a pharmaceutical carrier in accordance with known techniques. See, e.g., Remington, *The Science And Practice of Pharmacy* (9$^{th}$ Ed. 1995).

In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy consisting essentially of admixing the components, optionally including one or more accessory ingredients.

Formulations of the present invention suitable for nasal, parenteral, or inhalation administration comprise sterile aqueous and non-aqueous injection solutions of the active compound, which preparations are preferably isotonic with the blood of the intended recipient. These preparations may contain anti-oxidants, buffers, bacteriostats and solutes, which render the formulation isotonic with the blood of the intended recipient. Aqueous and non-aqueous sterile suspensions may include suspending agents and thickening agents. The formulations may be presented in unit dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active compound, in a unit dosage form in a sealed container. The compound or salt is provided in the form of a lyophilizate, which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent that is physiologically acceptable may be employed in sufficient quantity to emulsify the compound or salt in an aqueous carrier. One such useful emulsifying agent is phosphatidyl choline.

Other pharmaceutical compositions may be prepared from the compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to active compounds, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

The therapeutically effective dosage of any one active agent peptide will vary somewhat from compound to compound, and patient to patient (depending upon the age and condition of the subject), and will depend upon factors such as the age and condition of the patient and the route of delivery. Such dosages can be determined in accordance with routine pharmacological procedures known to those skilled in the art.

In general, the dose in the case of parenteral (e.g., intraveneous, subcutaneous) administration is typically in the range of 0.0001 or 0.001 to 50 or 100 mg/kg body weight. Supplemental or booster doses may be administered if desired.

The present invention is explained in greater detail in the following non-limiting Examples.

EXAMPLE 1

The Voltage-Dependent Anion Channel (VDAC) is a Receptor for Plasminogen Kringle 5 on Human Endothelial Cells We raised antibodies against peptides contained within both these regions and used them as probes to identify VDAC1 on the cell surface of HUVEC by flow cytometry. Receptor binding assays demonstrated that K5 binds with high affinity and to a large number of sites on the endothelial surface. K5 inhibits VEGF-4 stimulated HUVEC proliferation and induces a decrease in cytosolic pH. Highly purified VDAC1 binds to K5 after reconstitution of the receptor into liposomes. Our data suggest that VDAC1 is a receptor for K5 on the cell surface.

A. Materials and Methods

Materials. Culture media were purchased from life Technologies Inc. (Gaithersburg, Md.). Porcine pancreatic elastase, gastric mucosa pepsin, trypsin inhibitor and pre-formed liposomes were purchased from Sigma Chemical Co. (St. Louis, Mo.). Recombinant VEGF was purchased from Calbiochem (San Diego, Calif.). Endothelial cell growth supplement (ECGS) was purchased from Collaborative Research Inc. (Waltham, Mass.). $^{125}$I-labeled Bolton Hunter reagent for protein iodination was obtained from New England Nuclear (Boston, Mass.). The 21 amino acid peptides EINNTDLISLEYKYVLKKGEK ($Glu_{263}$-$Lys_{283}$, SEQ ID NO: 2) of SK and KVNNSSLIGLGYTQTLKPGIK ($Lys_{235}$-$Lys_{255}$, SEQ ID NO: 3) of VDAC1 were purchased from Research Genetics (Huntsville, Ala.). Fura-2/AM and [bis(carboxyethyl)-carbonyl fluorescein] (BCEF) were purchased from Molecular Probes, Inc. (Eugene, Oreg.). All other reagents were of the highest grade available.

Proteins. Human Pg was purified and separated into its two classes of isoforms, Pg 1 and Pg 2 as previously described [Deutsch and B. Mertz, Science 170, 1095 (1970); Gonzalez-Gronow and Robbins, Biochemistry 23, 190 (1984)]. Pg 2 was digested overnight with elastase and the mixture was fractionated by gel and affinity chromatography methods to obtain mini-Pg, followed by digestion of mini-Pg with pepsin to obtain K5 as previously described [Sottrup-Jensen et al., Prog. Chem. Fibrinol. Thrombol. 3, 191 (1978); Thewes et al., Biochim Biophys. Acta 912, 254 (1987)]. The sample was analyzed by gel electrophoresis (10-20% gradient gel, non-reducing conditions), appearing as a doublet of ~12 kDa, and it was identified by mass spectrometry as K5. Amino terminal sequence analysis of the protein by the Edman degradation method 5 resulted in the sequence LPTVETPSEE (SEQ ID NO: 4), corresponding to amino acids 450-459 of human Pg, thereby confirming that the purified plasminogen fragment was K5 [Petersen et al., J Biol. Chem. 265, 6104 (1990)].

Reduction/alkylation of K5 was performed by incubating 20 μg of the protein with 1 mM dithiothreitol for 30 min followed by incubation with 5 mM iodoacetamide for 30 min, both at room temperature, and removal of these reagents by exhaustive dialysis versus 10 mM Hepes, pH 7.5. Iodination of K5 was carried out using $^{125}$I labeled Bolton Hunter reagent according to the manufacturer's protocol. The specific activity varied from 500 to 700 cpm/mg.

Antibodies. Antibodies to SK were raised in rabbits according to standard protocols. The IgG fraction specific against the SK sequence $Glu_{263}$-$Lys_{283}$ was purified by immunoaffinity on a resin containing this peptide conjugated to activated Carboxyhexyl-(CH)-Sepharose (Amersham-Pharmacia, Piscataway, N.J.). Antibodies against the 21 amino acid sequence $Lys_{235}$-$Lys_{255}$ of VDAC1 conjugated to keyhole limpet hemocyanin [Kagen and Glick, in Methods of Hormone Radioimmunoassay, pp. 328-29 (eds. B. Jaffe and H. Behrman 1979)] were prepared in rabbits using standard protocols by COVANCE (Denver, Pa.). The IgG fraction specific to VDAC1 was purified by immunoaffinity on a resin containing the VDAC1 peptide conjugated to CH-Sepharose. The monoclonal antibody (mAb) 20B12 against human mitochondrial VDAC1 was purchased from Molecular Probes Inc. (Eugene, Oreg.).

Endothelial cell proliferation assay. Primary HUVEC were obtained from Clonetics (San Diego, Calif.) and grown as described in DMEM medium supplemented with 20% bovine serum, 100 U/ml penicillin/streptomycin, 2.5 μg/ml amphotericin B, 2 mM glutamine, 5 U/mil sodium heparin, and 200 μg/ml ECGS [Morales et al., Circulation 91, 755 (1995)]. Cells were washed with PBS and dispersed with a 0.05% solution of trypsin. Cells were resuspended in growth medium at a density of $25 \times 10^3$ cells/ml and 6 plated in 96-well culture plates (0.2 ml/well). After 24 h of incubation at 37° C., the media was replaced with 0.2 ml of DMEM, 5% bovine serum, 1% antibiotics and the test samples were applied. Cell proliferation was determined at 24 h using a BrdU labeling and colorimetric immunoassay detection method (Roche Molecular Biochemicals, NJ). Results were expressed as percent of control proliferation determined in the presence of VEGF (10 ng/ml) and the absence of K5.

Flow cytometry. HUVEC were detached from the culture flasks (75 cm2) by incubation for 5 min at 37° C. with $Ca^{2+}$- and $Mg^{2+}$-free PBS containing 4 mM EDTA, and then pelleted. Cells were washed once with PBS before resuspension in ice-cold Phenol Red-free Hanks' balanced salt solution (HBSS), 1% bovine serum albumin (BSA), 0.3 mg/ml goat IgG, and 0.01% $NaN_3$ (staining buffer) at a concentration of $1\times10^7$ cells/ml. Aliquots (100 µl) of cell suspensions were incubated for 30 min with appropriate dilutions of rabbit polyclonal anti-human SK peptide IgG, anti-human VDAC1 peptide IgG, or the murine anti-human mitochondrial VDAC1 mAb. Cells were washed with ice-cold staining buffer pelleted and resuspended in 100 µl ice-cold staining buffer. The cell suspensions were incubated in the dark with an AF488-conjugated for 30 mil with goat antirabbit or mouse IgG which was obtained from Molecular Probes, Inc. Then, cells were washed two times with ice-cold staining buffer, resuspended in ice-cold 1% paraformaldehyde and stored in the dark at 4° C. until analysis by flow cytometry (FACS). The mean relative fluorescence after excitation at a wavelength of 495 nm was determined for each sample on a FACSVantage SE flow cytometer (Becton-Dickinson, Franklin Lakes, N.J.) and analyzed with CELLQUEST® software (Becton-Dickinson).

Ligand binding analysis. Cells were grown in tissue culture plates until the monolayers were confluent. The cells were washed in HBSS. All binding assays were performed at 4° C. in RPMI 1640 containing 2% BSA. Increasing concentrations of 125I-K5 was incubated with cells for 60 min in 96-well strip plates. Free ligand was separated from bound ligand by aspirating the incubation mixture and washing the cell monolayers rapidly three times with RPMI 1640 containing 2% BSA. Wells were stripped from the plates and radioactivity was determined. Molecules of ligand bound were calculated after substraction of nonspecific binding measured in the presence of 50 mM p-aminobenzamidine. The dissociation constant ($K_d$) and maximal binding of K5 ($B_{max}$) were determined by fitting data directly to the Langmuir isotherm using the statistical program SYStat® for Windows.

Measurements of intracellular free Ca2+concentration and cytosolic pH. Intracellular free $Ca^{2+}$ concentration, $[Ca^{2+}]_i$, in HUVEC was measured by digital imaging microscopy using the fluorescent indicator Fura 2/AM [Gonzalez-Gronow et al., *J. Biol. Chem.* 268, 20791 (1993)]. For measurements of intracellular pH, HUVEC were incubated overnight in DMEM medium on glass cover slips as described above and then washed with HBSS with 0.1 M sodium bicarbonate, pH 7.1. Cells were then incubated for 20 min with 2 µM BCECF in HBSS, rinsed with buffer three times and placed on the fluorescent microscope stage. Intracellular pH, $[pH]_i$, was measured by a digital video imaging technique in cells stimulated by the ligands which were added after obtaining a stable baseline as previously described [Prpic et al., *Science* 244, 469 (1989)].

Gel electrophoresis. Electrophoresis was performed on polyacrylamide gels (1.2 mm thick, 14 cm×10 cm) containing 0.1% SDS. A discontinuous Laemli buffer system was used [Laemli, *Nature* 227, 680 (1970)]. Visualization of proteins was carried out by staining the gel with 0.25% Coomassie Brilliant Blue R-250 In 45% (v/v) methanol/10% (v/v) acetic acid. Transfer to nitrocellulose membranes was carried out by the Western blot method [Towbin et al., *Proc. Natl. Acad. Sci. U.S.A.* 76, 4350 (1979)]. The dye-conjugated Mr markers (Bio-Rad, Richmond, Calif.) used were carbonic anhydrase ($M_r$ 38,100), soybean trypsin inhibitor ($M_r$ 28,400), lysozyme ($M_r$ 18,200), aprotinin ($M_r$ 9,200) and insulin ($M_r$ 4,300).

Purification of VDAC1 from 1-LN cells. Human 1-LN prostate tumor cells were employed as a source of VDAC because it is difficult to obtain large numbers of endothelial cells in culture and we found that 1-LN cells are a good source for this protein. 1-LN cell lines were grown in RPMI 1640 supplemented with 10% (v/v) fetal bovine serum, 100 U/ml penicillin G and 100 ng/ml streptomycin. Cells grown in 20 culture flasks (150 $cm^2$) were detached with 10 mM EDTA in HBSS and pelleted by centrifugation. The cell pellet was suspended in 10 ml of 20 mM Hepes, pH 7.2, containing 0.25 M sucrose and the following proteinase inhibitors (each at 0.5 mg/ml): antipapain, bestatin, chymostatin, trans-epoxysuccinyl-L-leucylamido-(4-guanidino) butane (E-64), leupeptin, pepstatin, o-phenanthroline and aprotinin. Cells were lysed by sonication on ice (five 10 s bursts with 30 s intervals). All procedures were performed at 4° C. The homogenate was centrifuged at 800×g for 15 min to remove unbroken cells and nuclei, followed by centrifugation at 50,000×g for 1 h. The pellet containing cell membranes was resuspended in 20 mM Tris-HCl, pH 8.0, containing 1% (v/v) Triton X-100 to solubilize membranes and centrifuged again at 50,000×g for 30 min to remove insoluble materials. The VDAC receptor was sequentially purified to homogeneity using gel filtration on Sephadex G-150 and immunoaffinity chromatography with an anti-VDAC peptide IgG conjugated to Sepharose 4-B (data not shown).

Incorporation of VDAC1 into liposomes and binding of K5 to the reconstituted receptor. Purified VDAC1 was reconstituted into liposomes [Lichtenberg and Barenholz in *Methods in BiochemicalAnalysis*, pp. 337-462 (ed. D. Glick 1988); Barenholz and Amsalen, in *Liposome Technology*, pp 517-616 (ed.D. Gregoriadis 1993)] as follows: 50 µl of a suspension of liposomes (8 µM L-α.phosphatidylcholine, 8 µM β-oleoyl-γ-palmitoyl and 6.9 µM cholesterol) in 5% DMSO were mixed with VDAC1 (5 µg) and incubated with agitation for 30 min at room temperature. The concentration of DMSO was reduced to 0.5% with 50 mM Tris-HCl, pH 7.5. After addition of $^{125}$IK5 (10 nM) and incubation for another 30 min at room temperature, the mixture was filtered through a Sephadex G-75 column (55 cm×2 cm). To study inhibition of K5 binding to VDAC1 reconstituted into liposomes, the mixture was incubated with the specific anti-VDAC1 IgG for 30 min at room temperature before addition of $^{125}$I-K5.

RESULTS AND DISCUSSION

Analyses of sequence similarities between streptokinase and human VDAC1. Regions of sequence similarity between streptokinase and human VDAC1 were identified by the basic local alignment search tool (BLAST) provided by the Swiss Institute of Bioinformatics (SIB) (FIG. 1A). The topology prediction for helical transmembrane proteins was solved with use of the hidden Markov model (HMM), also provided by the SIB, and shows a loop through the outer mitochondrial membrane spanning VDAC1 residues $Q_{248}TLKPGIKL_{256}$ (FIG. 1B. SEQ ID NO: 5). We raised antibodies to the SK peptide $E_{263}INNTDLISLEYKYVLKKGEK_{283}$ (SEQ ID NO: 2) and the VDAC1 peptide $K_{236}VNNSSLIGLGYTQTLKPGIK_{255}$ (SEQ ID NO: 3) in rabbits, as described under Materials and Methods. VADC1 was purified to homogeneity as described under Materials and Methods (data not shown). A Coomassie Brilliant Blue R-250 stain of the electrophoresed material (data not shown) shows a major protein band in the Mr~32,000 size range. A blot binding assay with a rabbit anti-VDAC1 (peptide $Lys_{235}$-Lys255) IgG shows reactivity with this protein (data not shown). Similarly, the purified VDAC1 showed reactivity with the anti-SK (peptide $Glu_{263}$-$Lys_{283}$) IgG (data not shown), thereby confirming the structural relatedness between VDAC1 and SK. However, the purified VDAC1 did not show any reactivity with $^{251}$I-K5 when electroblotted to a nitrocellulose membrane (data not shown), suggesting that the affinity of solubilized VDAC1 for this ligand is lower than that of a receptor that is still bound to its membrane.

Figure 2:
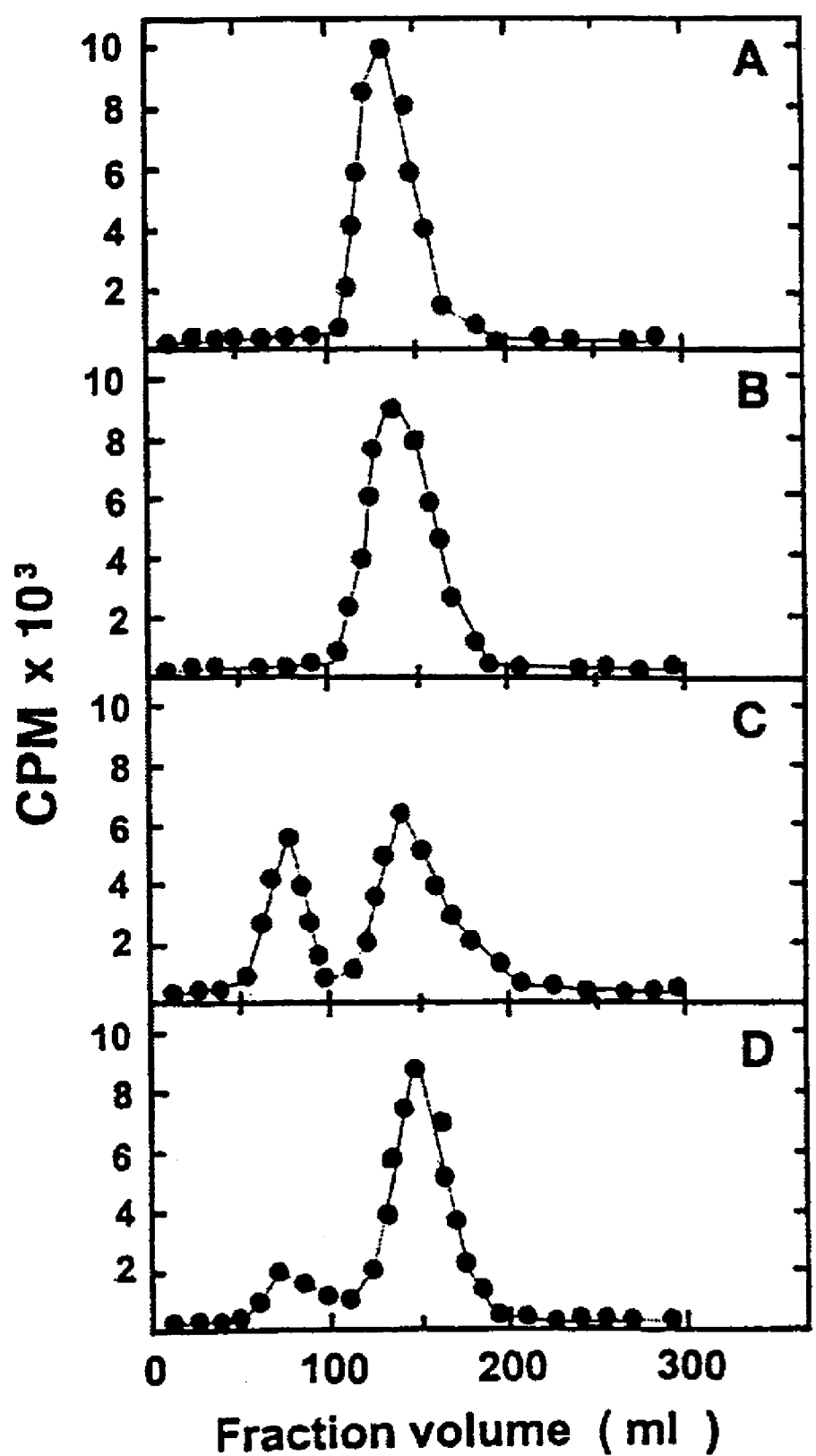
FIG. 2. Binding of K5 to VDAC1 incorporated into liposomes. All experiments were performed by gel filtration on a Sephadex G-75 column (55 cm×2 cm) equilibrated with 50 mM Tris-HCl, pH 7.5, at room temperature, as described under Materials and Methods.

Binding of K5 to VDAC1 incorporated into liposomes. The experiments described above demonstrate a significant impact on the ability of purified receptor to bind to K5; therefore, the purified VDAC1 was incorporated into liposomes and gel filtration on Sephadex G-75 employed to identify and separate the reactants (FIG. 2). $^{125}$I-K5 (30 ng) eluted between a column volume of 100-120 ml (FIG. 2A).

When a similar amount of $^{125}$I-K5 was incubated with solubilized VDAC1 (2 µg) and then filtered through the same column, all the radiolabeled material eluted in the same fractions as above, thereby suggesting no reactivity between K5 and the solubilized receptor (FIG. 2B). When VDAC1 was incorporated into liposomes and then reacted with K5, the radiolabeled material eluted from the column as two peaks, one of them corresponding to the void volume where VDAC1 elutes, and the other to the elution volume of unreacted K5 (FIG. 2C). These data indicate that K5 binds to VDAC1 when this receptor is incorporated into a lipid membrane. Binding of K5 to membrane-incorporated VDAC1 was inhibited by anti-VDAC1 (peptide $Lys_{235}$-$Lys_{255}$). IgG, suggesting again that this is the region responsible for binding to K5 (FIG. 2D).

Figure 3:
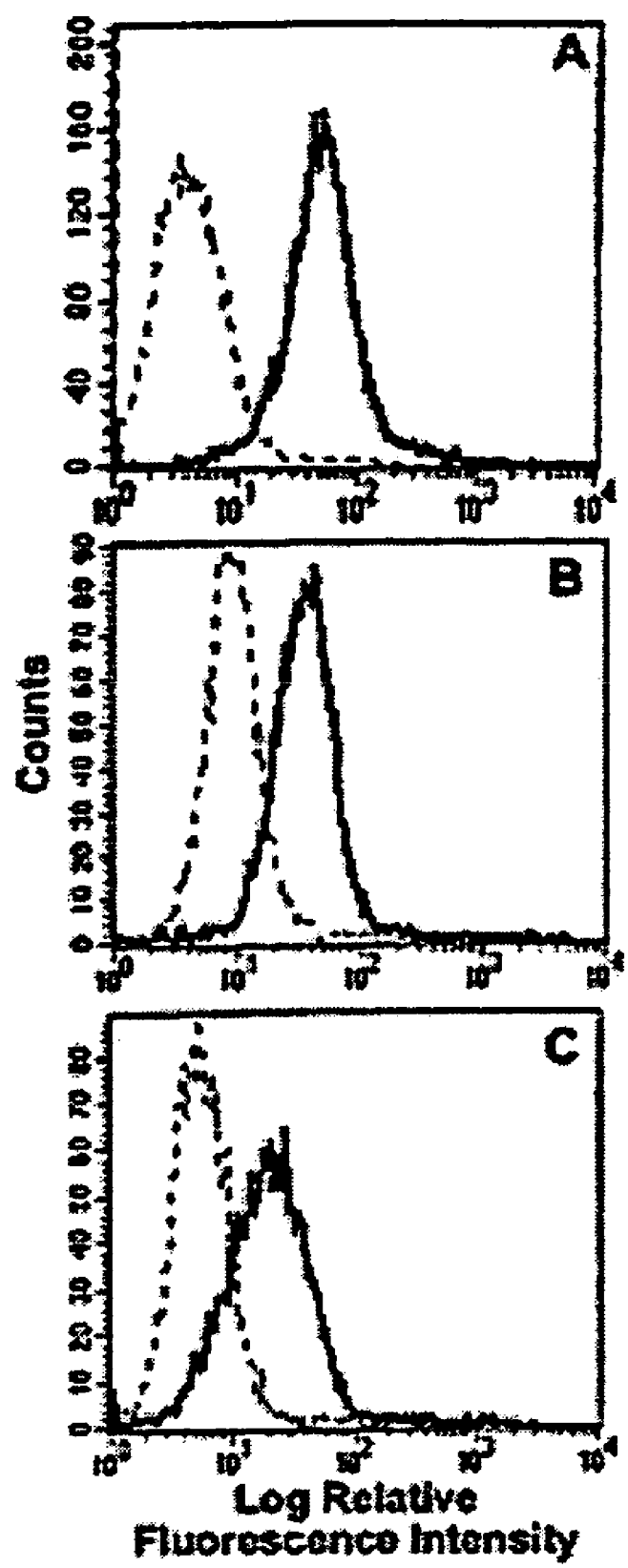
FIG. 3. Binding of antibodies directed against VDAC1 on the surface of HUVEC. Cells were analyzed by FACScan flow cytometry as described under Materials andMethods. Solid lines represent cells incubated with the antibodies directed against VDAC1 and dashed lines secondary antibody only.

Analyses of VDAC1 on the cell surface of HUVEC by flow cytometry. VDACs are a group of proteins that form channels through the outer mitochondrial membrane [Benz, *CRC Crit. Rev. Biochem.* 19, 145 (1985); Jan and Jan, *Cell* 56, 13 (1989)] and are also observed in human skeletal muscle, B lymphocyte, and hematopoietic cell plasma membranes [Jurgens et al., *Biol. Chem. Hoppe-Seyler* 372, 455 (1991); Bathori et al., *J. Biol. Chem.* 274, 29607 (1999)]. The expression of VDAC1 in plasma membranes of HUVEC has not been strictly analyzed. As determined by FACS, HUVEC reacted with an antibody against the SK peptide (FIG. 3A) as well as an antibody against the VDAC1 peptide (FIG. 3B) or a murine antibody against human mitochondrial VDAC1 (FIG. 3C), which is not surprising since mitochondrial and plasma membrane VDAC1 share the same primary structure [Jurgens et al., supra].

Figure 4:
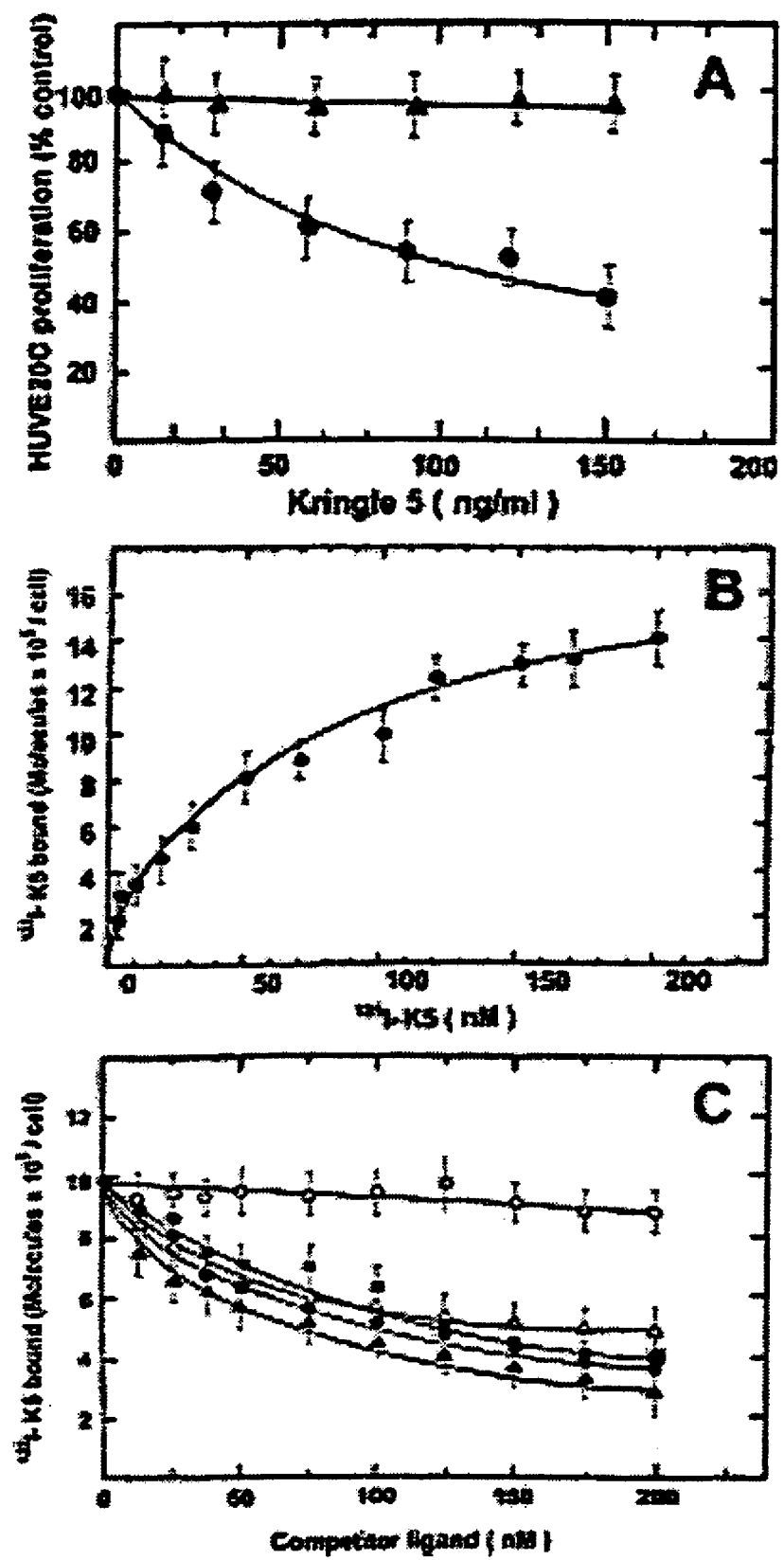
FIG. 4A. Anti-endothelial cell proliferative activity. K5 purified from pepsin digestion of human mini-Pg was assayed on HUVEC as described under Materials and Methods. Increasing concentrations of native K5 (filled circles) and reduced/alkylated K5 (filled triangles) were assayed in the presence of VEGF (10 ng/ml) in a 24 h proliferation assay. The inhibitory effect of K5 is expressed as a percentage of control cells grown only in the presence of VEGF.
FIG. 4B. Binding of K5 to HUVEC. Increasing concentrations of $^{125}$I -K5 were added to HUVEC cell monolayers (2×10$^4$ cells/well). Molecules of ligand bound were calculated after substraction of nonspecific binding measured in the presence of 50 mM p-amino-benzamidine as described under Materials and Methods. Data represent means ±S.D. from experiments performed in triplicate.
FIG. 4C. Inhibition of binding of K5 to HUVEC. $^{125}$I-K5 (100 nM) was incubated with increasing concentrations of nonlabeled Pg 2 (filled triangles), K 1-3 angiostatin (open circles), mini-Pg (open triangles), K5 (stars) or anti-VDAC1 (peptide $Lys_{235}$-$Lys_{255}$) IgG (squares). Data represent means ±S.D. from experiments performed in triplicate.

Inhibition of endothelial cell proliferation by K5. K5 was assayed for its inhibitory activity on HUVEC proliferation stimulated by VEGF (10 ng/ml). K5 inhibited HUVEC proliferation in a dose-dependent manner (FIG. 4A). As previously observed [Cao et al., *J. Biol. Chem.* 272, 22924 (1997)], the anti-endothelial cell proliferation of K5 was abolished after reduction/alkylation of the protein, suggesting that the formation of appropriate disulfide bridges is essential to maintain its activity.

Binding of K5 to HUVEC. K5 binds to these cells in a dose-dependent manner with high affinity (Kd of 28 nM) and to a large number of sites (12.6×10$^5$ binding sites/cell) (FIG. 4B). Binding of K5 to HUVEC can be inhibited by Pg, Pg peptides containing K5, and also by an IgG fi-action against a VDAC1 peptide showing structural relatedness to SK (FIG. 4C). Recently, another group performed a receptor-binding assay on endothelial cells using $^{125}$I-K5 [Gao et al., *J. Biol.Chem.* 277, 9492 (2002)]; however, no specific binding of K5 to endothelial cells was detected [Id.]. We obtained similar negative results when we used iodination techniques producing modifications of tyrosine residues of K5. The integrity of $Tyr_{512}$ of Pg is required for reactivity of K5 with its ligands [Thewes et al., *J. Biol.Chem.* 265, 3906 (1990)]. The same residue is also essential for the interaction of K5 with Pg residue $Lys_{50}$, which stabilizes Pg in a closed conformation when the protein is in the circulation [Ponting et al., *Biochem. Biophys. Acta*1159, 155 (1992)].

Effect of K5 binding on HUVEC [Ca2+]i and [pH]i. Endothelial cell proliferation is preceded by an increase in cytosolic pH, leading to angiogenesis and the repair of injured endothelial cells [Komatsu et al., *J. Pharmacol. Toxicol.* 41, 33 (1999)]. Cell proliferation is also dependent on modulation of extracellular Ca2+[Id.]. In order to understand the anti-proliferative effects of K5, we investigated whether binding of K5 to HUVEC produced any changes on $[Ca^{2+}]_i$ or $[pH]_i$, and compared these changes with those produced by the parent molecule, Pg 2, in the same cells. Addition of Pg (100 nM) to HUVEC induces a transient rise in $[Ca^{2+}]_i$ which lasts for 90 s returning to base line (FIG. 5A). The Pg 2-induced rise in $[Ca^{2+}]_i$ produced a rise in $[pH]_i$, which was continuous for 400 s (FIG. 5B). In contrast, a similar concentration (100 nM) of K5 did not significantly stimulate a rise in $[Ca^{2+}]_i$ (FIG. 5C), and produced a continuous decrease in $[pH]_i$ during the same time period (FIG. 5D). Incubation of HUVEC with K5 followed by Pg 2 shows a decreased stimulation in $[Ca^{2+}]_i$ (FIG. 5E); however, the decrease in $[pH]_i$ induced by K5 is abolished after addition of Pg (FIG. 5F). Table 1 summarizes these changes.

TABLE 1

Effects induced by Pg 2 and K5 on HUVEC*

| Ligand | Changes in $[Ca^{2+}]_i$ | Changes in $[pH]_i$ |
|---|---|---|
| Pg 2 | +450 nM | +0.17 |
| K5 | +100 nM | −0.20 |
| K5 + Pg 2 | +10 nM | ±0.07 |

Figure 5:
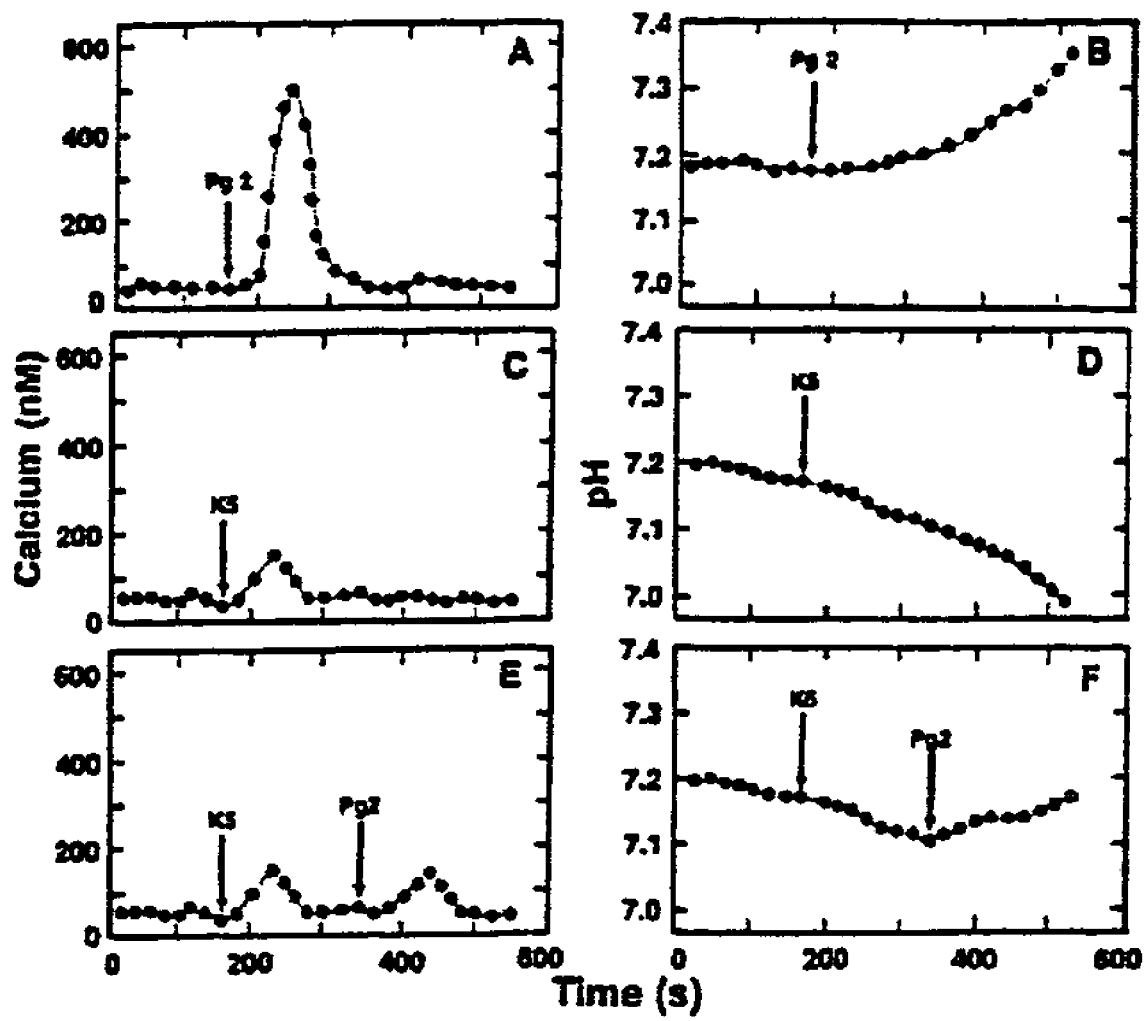
FIG. 5. Changes in intracellular Ca$^{2+}$ and pH on HUVEC exposed to Pg and K5. Cells were preloaded with Fura 2/AM (4 μM) or BCEF (2 μM) and changes in [Ca$^{2+}$]$_i$ or [pH]$_i$ were measured after addition of Pg 2 (100 nM) or K5 (100 nM), as described under Materials and Methods. Arrows indicate the times of addition of each ligand.

*These data were obtained from FIG. 5.

VDAC, which is well characterized in the mitochondrial outer membrane, binds and controls $Ca^{2+}$ transport into and from the mitochondria [Gincel et al., *Biochem J.* 358, 147 (2001)].

Without wishing to be bound to one theory of the invention, these data indicate that binding of K5 interfers with mechanisms controlling the influx of $Ca^{2+}$ into the cell via VDAC on the plasma membrane, leading to a decrease in $[pH]_i$. Interestingly, VDAC1 is concentrated in caveolae and caveolae-related domains of the plasma cell membrane

[Bathori et al., *J. Biol. Chem.*274, 29607 (1999)]. Caveolin-1 and 2 are abundantly expressed in normal human endothelial cells [Okamoto et al., *J. Biol. Chem.* 273, 5419 (1998)]. VEGF induces endothelial cell proliferation via a mechanism which produces a significant reduction in the expression of caveolin-1 [Liu et al., *J. Biol. Chem.* 274, 15781 (1999)]. In the absence of VEGF, angiostatin does not affect endothelial cell proliferation or alter the levels of expression of caveolin-1 in these cells [Id.]. However, in the presence of VEGF, angiostatin blocks the VEGF-induced down-regulation of caveolin-1 [Id.]. A large body of evidence points to caveolae as structures which cluster groups of fibrinolytic proteases, thus providing a favorable environment for protease cooperation. The urokinase-type plasminogen activator receptor, a GPI-linked protein, is localized in caveolae [Stahl and Mueller, *J. Cell Biol.* 129, 335 (1995)]. Receptors for Pg such as annexin II and the ganglioside GM1 are also localized in caveolae [Hajjar et al., *J. Biol. Chem.* 269, 21191 (1994); L. Miles et al., *Biochemistry* 28, 9337 (1989); R. Parton, *J. Histochem. Cytochem.* 42, 155 (1994)] along with metalloproteinase 2 [Puyraimond et al., *Exp. Cell Res.* 262, 28 (2001)]. Annexin II and the ganglioside GM1 bind Pg via the L-lysine binding site in K1, whereas VDAC binds Pg via a site in K5. In situ degradation of receptor-bound Pg by metalloproteinases may generate anti-angiogenic peptides (K 1-3 and K5) [Gately et al., *Cancer Res.* 56, 4887 (1996)] which once generated may control angiogenesis via alternative pathways.

EXAMPLE 2

Competition of SK and VDAC1 Peptides for Anti-SK IgG

Figure 6:
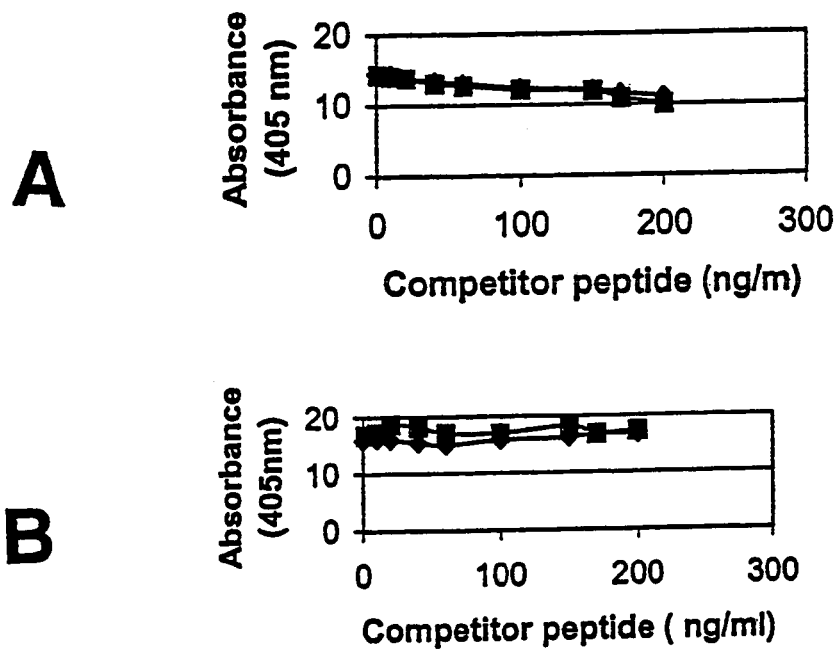
FIG. 6. Solid-phase bound SK, in 96-well culture plates, was reacted with anti-SK IgG (1 μg/ml) in the presence of the SK and VDAC1 peptides.

Culture plates coated with SK were reacted with a single concentration (1 µg/ml) of anti-SG IgG purified by affinity chromatography on a resin containing the SK peptide, $Glu_{263}$-$Lys_{283}$, conjugated to Sepharose 4B. Increasing concentrations of the SK ($Glu_{263}$-$Lys_{23}$) and VDAC1 ($Lys_{235}$-$Lys_{255}$) peptides were added to wells containing this antibody. As controls we used the polypeptides corresponding to the SK regions $Asp_{128}$-$Asp_{137}$ and $Asp_{382}$-$Ile_{392}$. The results show that both the structurally homologous SK and VDAC1 peptides compete with SK for the anti-SK IgG (FIG. 6A), whereas SK peptides from different regions of this molecule do not compete with SK for this antibody (FIG. 6B). This experiment suggests a close structural homology between SK and VDAC1 because the anti-SK IgG reacts with a similar specificity with both these peptides.

EXAMPLE 3

Effect of a Purified Anti-SK-peptide IgG on the Increase in Intracellular $Ca^{2+}$ Induced by K5 on Human Umbilical Vein Endothelial Cells (HUVEC)

Figure 7:
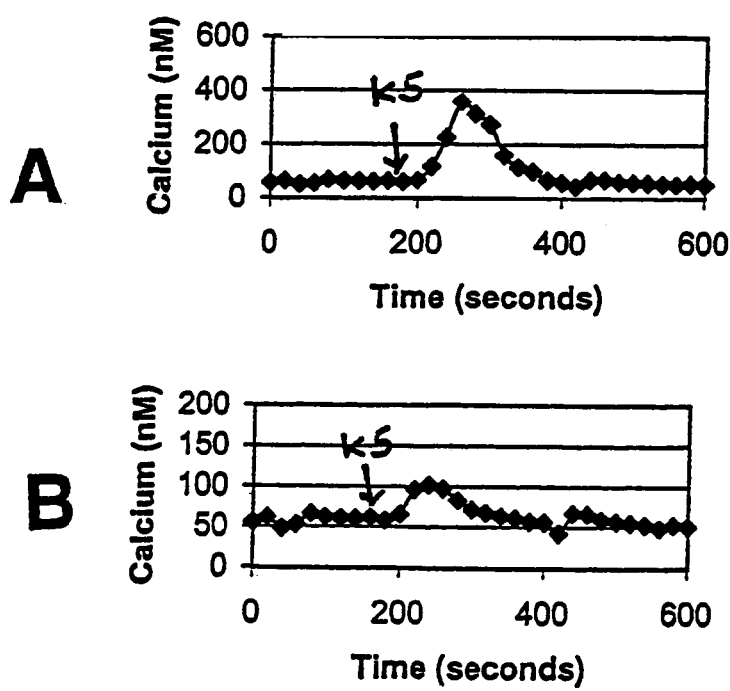
FIG. 7. Measurements of intracellular Ca$^{2+}$ on HUVECs.

HUVECs were incubated with K5 in the absence of anti-SK-peptide IgG. The results (FIG. 7A), demonstrate that additionof K5 (0.1 µM) at 180 s induce a rise in intracellular $Ca^{2+}$ which peaks at 260 s, followed by a return towards base line at 320 s. When HUVECs were pre-incubated with the anti-SK-peptide IgG (1 µg/ml), the rise in intracellular $Ca^{2+}$ after addition of K5 was inhibited (80%) (FIG. 7B), suggesting a close structural homology between SK and the corresponding K5 receptor (i.e. VDAC1) on the cell surface.

EXAMPLE 4

Figure 8:
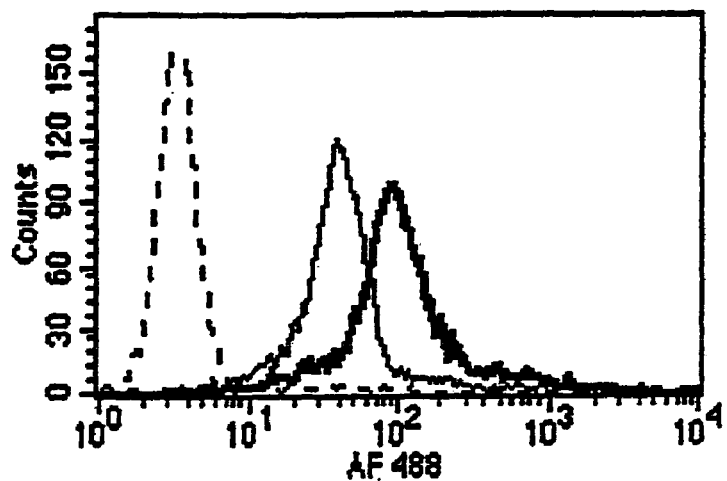
FIG. 8. Binding of anti-SK-peptide IgG to HUVEC is antagonized by mini-Pg, a K5 containing plasminogen region. The bold line refers to anti-sk, the solid line refers to mini-pg plus anti-sk, and the dotted line refers to secondary only.

Binding of Anti-SK-Peptide IgG to HUVEC is Antagonized by Mini-Pg, a K5 Containing Plasminogen Region HUVECs were reacted with the anti-SK-peptide ($Glu_{263}$-$Lys_{283}$) IgG in the absence or presence of mini-Pg, a K5 containing Pg fragment. FACS analyses of these cells show (FIG. 8) that the antibody is highly reactive with an epitope on the surface of the cells and this interaction can be blocked by mini-Pg, thereby suggesting that a region with affinity for K5, which is structurally homologous to SK, is expressed on the surface of HUVECs.

Examples 2-4 show that SK and VDAC1 are structurally and functionally related. They both bind plasminogen via its K5 region. Furthermore, the presence of VDAC1 on the surface of HUVEC indicates that K5 is a key element in the control of $Ca^{2+}$ homeostasis by these cells.

EXAMPLE 5

Effect of Antibodies Against Cell Surface Antigens on the Proliferation of Human Umbilical Vein Endothelial Cells This example illustrates the effect of antibodies against cell surface antigens (including antibodies of the present invention) on the proliferation of human umbilical vein endothelial cells. All antibodies were used at a single concentration (100 ng/ml) and incubated with the cells for 48 hrs. before measuring the effect on proliferation. Data are given in Table 2 below. Anti-$SK_{p-1}$ is the antibody against the region located between residues $Tyr_{252}$-$Lys_{283}$ in streptokinase, as described herein; Anti-$VDAC_{p-1}$ is the antibody against the region located between residues $Tyr_{224}$-$Lys_{255}$ in VDAC, as described herein; Anti-$SK_{p-2}$ is an antibody against the region located between residues $Leu_{43}$-$His_{49}$ in streptokinase; Anti-$SK_{whole}$ is an antibody prepared in rabbits against the whole streptokinase molecule; Anti-$VDAC_{p-2}$ is an antibody prepared in rabbits against the region located between residues $Asn_{185}$-$Lys_{197}$ in VDAC (This antibody was purchased from Affinity Bioreagents, Inc. (ABR), Golden, Colo., USA); and Anti-$VDAC_{mAb}$ is a monoclonal antibody against mitochondrial VDAC (purchased from Molecular Probes, Eugene, Oreg., USA). The two commercial antibodies have been reported in the literature as specific for VDAC, although their physiological activity has not been described.

TABLE 2

| Antibody | proliferation (%) |
|---|---|
| Anti-$SK_{p-1}$ | 98 ± 3.6 |
| Anti-$VDAC_{p-1}$ | 38 ± 5.1 |
| Anti-$SK_{p-2}$ | 97 ± 4.3 |
| Anti-$SK_{whole}$ | 98 ± 2.8 |
| Anti-$VDAC_{p-2}$ | 96 ± 3.1 |
| Anti-$VDAC_{mAb}$ | 98 ± 2.7 |

As can be clearly seen in Table 2, only the anti-VDACp-1 antibody is effective and in agreement with the other effects reported above.

The foregoing is illustrative of the present invention, and is not to be construed as limiting thereof. The invention is defined by the following claims, with equivalents of the claims to be included therein.

That which is claimed is:

1. A monoclonal antibody that binds to the human mitochondrial voltage-dependent anion channel protein of SEQ ID NO: 1 at an epitope between amino acids $Tyr_{224}$ through $Lys_{255}$ thereof.

2. The antibody according to claim 1, wherein said antibody inhibits the binding of human plasminogen kringle 5 to endothelial cells.

3. A pharmaceutical formulation comprising an antibody according to claim 1 in a pharmaceutically acceptable carrier.

4. The pharmaceutical formulation according to claim 3, wherein said carrier is an aqueous camer.

5. The antibody of claim 1, wherein said antibody is a humanized antibody.

* * * * *

UNITED STATES PATENT AND TRADEMARK OFFICE
CERTIFICATE OF CORRECTION

PATENT NO. : 7,276,588 B2 Page 1 of 1
APPLICATION NO. : 10/641340
DATED : October 2, 2007
INVENTOR(S) : Pizzo et al.

It is certified that error appears in the above-identified patent and that said Letters Patent is hereby corrected as shown below:

Column 42, Claim 4, Line 50: Please correct "camer"
To read -- carrier --

Signed and Sealed this

First Day of April, 2008

JON W. DUDAS
*Director of the United States Patent and Trademark Office*

SEQUENCE LISTING

<160> NUMBER OF SEQ ID NOS: 59

<210> SEQ ID NO 1
<211> LENGTH: 282
<212> TYPE: PRT
<213> ORGANISM: Homo sapiens
<220> FEATURE:
<221> NAME/KEY: MISC_FEATURE
<222> LOCATION: (1)..(282)
<223> OTHER INFORMATION: Human voltage-dependent anion channel isoform I

<400> SEQUENCE: 1

```
Ala Val Pro Pro Thr Tyr Ala Asp Leu Gly Lys Ser Ala Arg Asp Val
1               5                   10                  15

Phe Thr Lys Gly Tyr Gly Phe Gly Leu Ile Lys Leu Asp Leu Lys Thr
                20                  25                  30

Lys Ser Glu Asn Gly Leu Glu Phe Thr Ser Ser Gly Ser Ala Asn Thr
            35                  40                  45

Glu Thr Thr Lys Val Thr Gly Ser Leu Glu Thr Lys Tyr Arg Trp Thr
50                  55                  60

Glu Tyr Gly Leu Thr Phe Thr Glu Lys Trp Asn Thr Asp Asn Thr Leu
65                  70                  75                  80

Gly Thr Glu Ile Thr Val Glu Asp Gln Leu Ala Arg Gly Leu Lys Leu
                85                  90                  95

Thr Phe Asp Ser Ser Phe Ser Pro Asn Thr Gly Lys Lys Asn Ala Lys
            100                 105                 110

Ile Lys Thr Gly Tyr Lys Arg Glu His Ile Asn Leu Gly Cys Asp Met
        115                 120                 125

Asp Phe Asp Ile Ala Gly Pro Ser Ile Arg Gly Ala Leu Val Leu Gly
130                 135                 140

Tyr Glu Gly Trp Leu Ala Gly Tyr Gln Met Asn Phe Glu Thr Ala Lys
145                 150                 155                 160

Ser Arg Val Thr Gln Ser Asn Phe Ala Val Gly Tyr Lys Thr Asp Glu
                165                 170                 175

Phe Gln Leu His Thr Asn Val Asn Asp Gly Thr Glu Phe Gly Gly Ser
            180                 185                 190

Ile Tyr Gln Lys Val Asn Lys Lys Leu Glu Thr Ala Val Asn Leu Ala
        195                 200                 205

Trp Thr Ala Gly Asn Ser Asn Thr Arg Phe Gly Ile Ala Ala Lys Tyr
210                 215                 220

Gln Ile Asp Pro Asp Ala Cys Phe Ser Ala Lys Val Asn Asn Ser Ser
225                 230                 235                 240

Leu Ile Gly Leu Gly Tyr Thr Gln Thr Leu Lys Pro Gly Ile Lys Leu
                245                 250                 255

Thr Leu Ser Ala Leu Leu Asp Gly Lys Asn Val Asn Ala Gly Gly His
            260                 265                 270

Lys Leu Gly Leu Gly Leu Glu Phe Gln Ala
        275                 280
```

<210> SEQ ID NO 2
<211> LENGTH: 21
<212> TYPE: PRT
<213> ORGANISM: Artificial sequence
<220> FEATURE:
<223> OTHER INFORMATION: Synthetic polypeptide -continued

```
<400> SEQUENCE: 2

Glu Ile Asn Asn Thr Asp Leu Ile Ser Leu Glu Tyr Lys Tyr Val Leu
1               5                   10                  15

Lys Lys Gly Glu Lys
            20

<210> SEQ ID NO 3
<211> LENGTH: 21
<212> TYPE: PRT
<213> ORGANISM: Artificial sequence
<220> FEATURE:
<223> OTHER INFORMATION: Synthetic polypeptide

<400> SEQUENCE: 3

Lys Val Asn Asn Ser Ser Leu Ile Gly Leu Gly Tyr Thr Gln Thr Leu
1               5                   10                  15

Lys Pro Gly Ile Lys
            20

<210> SEQ ID NO 4
<211> LENGTH: 10
<212> TYPE: PRT
<213> ORGANISM: Homo sapiens
<220> FEATURE:
<221> NAME/KEY: MISC_FEATURE
<222> LOCATION: (1)..(10)
<223> OTHER INFORMATION: Amino acids 450-459 of human plasminogen

<400> SEQUENCE: 4

Leu Pro Thr Val Glu Thr Pro Ser Glu Glu
1               5                   10

<210> SEQ ID NO 5
<211> LENGTH: 9
<212> TYPE: PRT
<213> ORGANISM: Homo sapiens
<220> FEATURE:
<221> NAME/KEY: MISC_FEATURE
<222> LOCATION: (1)..(9)
<223> OTHER INFORMATION: Amino acids 248-256 of VDAC1

<400> SEQUENCE: 5

Gln Thr Leu Lys Pro Gly Ile Lys Leu
1               5

<210> SEQ ID NO 6
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 6

Asn Thr Leu Lys Pro Gly Ile Lys Leu
1               5

<210> SEQ ID NO 7
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 7

Gln Ser Leu Lys Pro Gly Ile Lys Leu
1               5
```

```
<210> SEQ ID NO 8
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 8

Gln Thr Ile Lys Pro Gly Ile Lys Leu
1               5

<210> SEQ ID NO 9
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 9

Gln Thr Leu Arg Pro Gly Ile Lys Leu
1               5

<210> SEQ ID NO 10
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 10

Gln Thr Leu Lys Gly Gly Ile Lys Leu
1               5

<210> SEQ ID NO 11
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 11

Gln Thr Leu Lys Pro Pro Ile Lys Leu
1               5

<210> SEQ ID NO 12
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 12

Gln Thr Leu Lys Pro Gly Leu Lys Leu
1               5

<210> SEQ ID NO 13
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 13

Gln Thr Leu Lys Pro Gly Ile Arg Leu
1               5
```

<210> SEQ ID NO 14
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 14

Gln Thr Leu Lys Pro Gly Ile Lys Ile
1               5

<210> SEQ ID NO 15
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 15

His Thr Leu Lys Pro Gly Ile Lys Leu
1               5

<210> SEQ ID NO 16
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 16

Lys Thr Leu Lys Pro Gly Ile Lys Leu
1               5

<210> SEQ ID NO 17
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 17

Glu Thr Leu Lys Pro Gly Ile Lys Leu
1               5

<210> SEQ ID NO 18
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 18

Ser Thr Leu Lys Pro Gly Ile Lys Leu
1               5

<210> SEQ ID NO 19
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 19

Gln Gln Leu Lys Pro Gly Ile Lys Leu
1               5

```
<210> SEQ ID NO 20
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 20

Gln Thr Val Lys Pro Gly Ile Lys Leu
1               5

<210> SEQ ID NO 21
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 21

Gln Thr Ala Lys Pro Gly Ile Lys Leu
1               5

<210> SEQ ID NO 22
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 22

Gln Thr Leu Gln Pro Gly Ile Lys Leu
1               5

<210> SEQ ID NO 23
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 23

Gln Thr Leu Lys Cys Gly Ile Lys Leu
1               5

<210> SEQ ID NO 24
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 24

Gln Thr Leu Lys Ser Gly Ile Lys Leu
1               5

<210> SEQ ID NO 25
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 25

Gln Thr Leu Lys Met Gly Ile Lys Leu
1               5
```

```
<210> SEQ ID NO 26
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 26

Gln Thr Leu Lys Pro Cys Ile Lys Leu
1               5

<210> SEQ ID NO 27
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 27

Gln Thr Leu Lys Pro Gly Val Lys Leu
1               5

<210> SEQ ID NO 28
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 28

Gln Thr Leu Lys Pro Gly Ala Lys Leu
1               5

<210> SEQ ID NO 29
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 29

Gln Thr Leu Lys Pro Gly Ile Gln Leu
1               5

<210> SEQ ID NO 30
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 30

Gln Thr Leu Lys Pro Gly Ile Lys Val
1               5

<210> SEQ ID NO 31
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 31

Gln Thr Leu Lys Pro Gly Ile Lys Ala
1               5
```

```
<210> SEQ ID NO 32
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 32

Asn Ser Leu Lys Pro Gly Ile Lys Leu
1               5

<210> SEQ ID NO 33
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 33

Asn Gln Leu Lys Pro Gly Ile Lys Leu
1               5

<210> SEQ ID NO 34
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 34

His Ser Leu Lys Pro Gly Ile Lys Leu
1               5

<210> SEQ ID NO 35
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 35

His Gln Leu Lys Pro Gly Ile Lys Leu
1               5

<210> SEQ ID NO 36
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 36

Ser Gln Leu Lys Pro Gly Ile Lys Leu
1               5

<210> SEQ ID NO 37
<211> LENGTH: 4
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: Amino acids 227-230 of VDAC1

<400> SEQUENCE: 37

Asp Pro Asp Ala
1
```

```
<210> SEQ ID NO 38
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 38

Glu Pro Asp Ala
1

<210> SEQ ID NO 39
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 39

Asp Gly Asp Ala
1

<210> SEQ ID NO 40
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 40

Asp Pro Glu Ala
1

<210> SEQ ID NO 41
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 41

Asp Pro Asp Val
1

<210> SEQ ID NO 42
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 42

Lys Pro Asp Ala
1

<210> SEQ ID NO 43
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 43

Arg Pro Asp Ala
1
```

```
<210> SEQ ID NO 44
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 44

Asp Cys Asp Ala
1

<210> SEQ ID NO 45
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 45

Asp Ser Asp Ala
1

<210> SEQ ID NO 46
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 46

Asp Met Asp Ala
1

<210> SEQ ID NO 47
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 47

Asp Pro Lys Ala
1

<210> SEQ ID NO 48
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 48

Asp Pro Arg Ala
1

<210> SEQ ID NO 49
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 49

Asp Pro Asp Ser
1
```

```
<210> SEQ ID NO 50
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 50

Glu Gly Asp Ala
1

<210> SEQ ID NO 51
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 51

Asp Pro Glu Ser
1

<210> SEQ ID NO 52
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 52

Glu Pro Glu Ala
1

<210> SEQ ID NO 53
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 53

Asp Ser Glu Ala
1

<210> SEQ ID NO 54
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 54

Glu Pro Asp Ser
1

<210> SEQ ID NO 55
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 55

Asp Gly Asp Ser
1
```

```
<210> SEQ ID NO 56
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 56

Asp Pro Glu Val
1

<210> SEQ ID NO 57
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 57

Arg Gly Asp Ala
1

<210> SEQ ID NO 58
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 58

Arg Pro Glu Ala
1

<210> SEQ ID NO 59
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 59

Arg Pro Asp Ser
1
```